United States Patent
Noguchi

(10) Patent No.: US 11,484,293 B2
(45) Date of Patent: Nov. 1, 2022

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Masafumi Noguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 641 days.

(21) Appl. No.: 16/535,896

(22) Filed: Aug. 8, 2019

(65) Prior Publication Data

US 2020/0100770 A1   Apr. 2, 2020

(30) Foreign Application Priority Data

Sep. 27, 2018   (JP) .............................. JP2018-181875

(51) Int. Cl.
 *A61B 8/08* (2006.01)
 *G06T 7/00* (2017.01)
 (Continued)

(52) U.S. Cl.
 CPC .......... *A61B 8/5246* (2013.01); *A61B 5/0053* (2013.01); *A61B 8/14* (2013.01);
 (Continued)

(58) Field of Classification Search
 None
 See application file for complete search history.

(56) References Cited

U.S. PATENT DOCUMENTS

2008/0269605 A1   10/2008   Nakaya
2012/0253195 A1*  10/2012   Inoue .................. G01S 7/52036
                                                      600/438

(Continued)

FOREIGN PATENT DOCUMENTS

JP   2008-272025 A   11/2008
JP   2017-12598 A    1/2017

OTHER PUBLICATIONS

Extended European Search Report, dated Jan. 24, 2020, for corresponding European Application No. 19189562.2.

(Continued)

*Primary Examiner* — Amelie R Davis
*Assistant Examiner* — Marjan Saboktakin
(74) *Attorney, Agent, or Firm* — Birch, Stewart, Kolasch & Birch, LLP

(57) ABSTRACT

An ultrasound diagnostic apparatus includes an ultrasound probe, a reference image holding unit that holds an ultrasound image acquired by fixing a position of the ultrasound probe as a reference image, a movement vector calculation unit that calculates a movement vector between two ultrasound images, a movement vector integration unit that integrates the movement vector from a time when the reference image is held to a current time, a deformed image generation unit that generates a deformed image in which the current ultrasound image is moved and changed to a time when the reference image is held based on an integration result, a tomographic plane determination unit that compares the deformed image with the reference image to determine whether tomographic planes of the current ultrasound image and the reference image are the same as each other, and a determination result notification unit that notifies a user of a determination result.

20 Claims, 11 Drawing Sheets

(51) Int. Cl.
  *G06T 7/246*  (2017.01)
  *A61B 5/00*  (2006.01)
  *A61B 8/14*  (2006.01)
  *A61B 8/00*  (2006.01)

(52) U.S. Cl.
  CPC .............. *A61B 8/463* (2013.01); *A61B 8/467* (2013.01); *A61B 8/5207* (2013.01); *A61B 8/5223* (2013.01); *A61B 8/54* (2013.01); *G06T 7/0014* (2013.01); *G06T 7/248* (2017.01); *G06T 7/97* (2017.01); *G06T 2207/10132* (2013.01); *G06T 2207/20092* (2013.01); *G06T 2207/30008* (2013.01); *G06T 2207/30101* (2013.01)

(56) References Cited

U.S. PATENT DOCUMENTS

2017/0196532 A1   7/2017  Choi
2019/0216441 A1*  7/2019  Matsumoto ............. G06T 7/246

OTHER PUBLICATIONS

European Office Action, dated Sep. 11, 2020, for corresponding European Application No. 19189562.2.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

The present application claims priority under 35 U.S.C. § 119 to Japanese Patent Application No. 2018-181875, filed on Sep. 27, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and particularly, to an ultrasound diagnostic apparatus and a method of controlling an ultrasound diagnostic apparatus that are used for a compression test of a subject.

2. Description of the Related Art

In the related art, an ultrasound diagnostic apparatus has been known as an apparatus that obtains an image of the inside of a subject. Generally, the ultrasound diagnostic apparatus comprises an ultrasound probe provided with an oscillator array in which a plurality of elements are arranged. In a state where the ultrasound probe is brought into contact with a body surface of the subject, an ultrasound beam is transmitted from the oscillator array toward the inside of the subject, ultrasonic echoes from the subject are received by the oscillator array, and element data are acquired. Moreover, the ultrasound diagnostic apparatus processes the obtained element data electrically, and generates an ultrasound image for a relevant part of the subject.

It is generally performed that a blood vessel of the subject is observed using such an ultrasound diagnostic apparatus, and the presence or absence of a thrombus in the blood vessel is inspected. As a disease related to the thrombus in the blood vessel, for example, a so-called deep vein thrombosis (DVT) is known. The DVT is a disease that a thrombus occurs in a deep vein, and often occurs in a lower thigh.

Although a normal deep vein in which the thrombus is not present is easily deformed by compression, the deep vein in which the thrombus has occurred is not easily deformed by the compression. Therefore, as a method of inspecting the DVT that has occurred in the lower thigh using the ultrasound diagnostic apparatus, for example, so-called compression test method of observing a cross section of the compressed deep vein while compressing the deep vein having a concern that the DVT may occur is known.

For the ultrasound diagnostic apparatus, various measures are made in order to accurately perform such a compression test. For example, JP2008-272025A discloses an ultrasound diagnostic apparatus that, in order to easily observe the deformation of the deep vein, automatically specifies an ultrasound image in which a contact pressure between an ultrasound probe and a subject is maximized and an ultrasound image in which a deep vein is not deformed by a compression test, and displays the ultrasound images side by side.

SUMMARY OF THE INVENTION

Meanwhile, in general, an observation target such as a blood vessel is compressed by pressing an ultrasound probe against a body surface of a subject in a compression test. However, in this case, inclination, position, and the like of the ultrasound probe may shift. In this case, even in a case where the ultrasound diagnostic apparatus disclosed in JP2008-272025A is used, there are problems in that accurate diagnosis is difficult such that different tomographic planes may be observed before and after the compression, and a thrombus that is locally present in a blood vessel may be overlooked.

The present invention has been made in order to solve such related-art problems, and an object thereof is to provide an ultrasound diagnostic apparatus and a method of controlling an ultrasound diagnostic apparatus that allow a user to perform accurate diagnosis in a compression test.

In order to achieve the above object, an ultrasound diagnostic apparatus of the present invention is an ultrasound diagnostic apparatus that has an ultrasound probe and is used to compression-test an observation target in a subject by pressing the ultrasound probe against a body surface of the subject, the ultrasound diagnostic apparatus comprising: an image acquisition unit that performs transmission of an ultrasound beam from the ultrasound probe toward the subject to acquire ultrasound images sequentially and consecutively; a display unit that displays the ultrasound image acquired by the image acquisition unit; a reference image holding unit that holds the ultrasound image acquired by the image acquisition unit in a state where a position of the ultrasound probe is fixed in order to depict a tomographic plane of the observation target on the display unit as a reference image; a movement vector calculation unit that calculates a movement vector indicating an image movement change between two ultrasound images that are consecutive for each predetermined number of frames among the ultrasound images sequentially acquired by the image acquisition unit; a movement vector integration unit that integrates the movement vectors that are respectively calculated by the movement vector calculation unit in the ultrasound images from a time when the reference image is held by the reference image holding unit to a current time; a deformed image generation unit that generates a deformed image in which the ultrasound image of a current frame acquired by the image acquisition unit is moved and changed tracing back to a time when the reference image is held by the reference image holding unit based on a movement change integrated by the movement vector integration unit; a tomographic plane determination unit that determines whether a tomographic plane of the subject depicted from the ultrasound image of the current frame and a tomographic plane of the subject depicted from the reference image are the same as each other by comparing the deformed image generated by the deformed image generation unit with the reference image held by the reference image holding unit; and a determination result notification unit that notifies a user of a determination result obtained by the tomographic plane determination unit.

The movement vector calculation unit may calculate a movement change of each pixel in the ultrasound image as the movement vector.

In this case, it is preferable that the movement vector integration unit integrates the movement vector for each pixel with respect to the ultrasound images of a plurality of frames acquired by the image acquisition unit, and the deformed image generation unit generates the deformed image by moving and changing each pixel in the ultrasound image of the current frame tracing back to a time when the reference image is held by the reference image holding unit based on a movement change integrated by the movement vector integration unit.

Alternatively, the movement vector calculation unit may calculate a movement change of a high-luminance pixel of which a luminance is equal to or more than a predetermined threshold value among all the pixels in the ultrasound image as the movement vector.

In this case, it is preferable that the movement vector integration unit integrates the movement vector for each high-luminance pixel with respect to the ultrasound images of a plurality of frames acquired by the image acquisition unit, and the deformed image generation unit generates the deformed image based on a movement change of each high-luminance pixel in the ultrasound image of the current frame.

Alternatively, the movement vector calculation unit may partition the ultrasound images adjacent to each other in time series into a predetermined number of regions, respectively, and may calculate a movement change of one pixel in each of the regions as the movement vector of the region.

In this case, it is preferable that the movement vector integration unit integrates the movement vector for each of the regions partitioned by the movement vector calculation unit in the ultrasound images of the plurality of frames acquired by the image acquisition unit, and the deformed image generation unit generates the deformed image based on a movement change of each of the regions in the ultrasound image of the current frame. Moreover, the tomographic plane determination unit may compare the deformed image with the reference image for each region partitioned by the movement vector calculation unit to determine the tomographic plane of the subject, and the determination result notification unit may notify the user of the determination result for each partitioned region obtained by the tomographic plane determination unit.

Additionally, the tomographic plane determination unit may perform image analysis with respect to the deformed image and the reference image to calculate a similarity between the deformed image and the reference image, and may determine the tomographic plane of the subject based on the calculated similarity.

In this case, the determination result notification unit may superimpose the determination result obtained by the tomographic plane determination unit on the ultrasound image of the current frame to display the superimposed image on the display unit.

Additionally, the ultrasound diagnostic apparatus may further comprise a mask image generation unit that performs image analysis with respect to the deformed image generated by the deformed image generation unit and the reference image held by the reference image holding unit to detect at least one of muscle fibers or a bone, and generates a mask image in which regions other than the muscle fibers and the bone respectively detected with respect to the deformed image and the reference image are masked.

In this case, it is preferable that the tomographic plane determination unit determines the tomographic plane of the subject by comparing the mask image for the deformed image with the mask image for the reference image.

Alternatively, the ultrasound diagnostic apparatus may further comprise a mask image generation unit that performs image analysis with respect to the ultrasound images, which are sequentially and consecutively acquired by the image acquisition unit to detect at least one of muscle fibers or a bone, and generates a mask image in which regions other than the muscle fibers and the bone detected with respect to the ultrasound image are masked, in which the reference image holding unit may hold the mask image generated by the mask image generation unit at a time when the position of the ultrasound probe is fixed in order to depict the tomographic plane of the observation target on the display unit, as the reference image, the movement vector calculation unit may calculate an image movement change in the mask image as the movement vector, and the deformed image generation unit may generate the deformed image in which the ultrasound image of the current frame is moved and changed tracing back to the time when the reference image is held by the reference image holding unit based on a movement change of at least one of the muscle fibers or the bone integrated by the movement vector integration unit.

In this case, it is preferable that the tomographic plane determination unit determines the tomographic plane of the subject by comparing the deformed image with a mask image held as the reference image.

Additionally, the ultrasound diagnostic apparatus may further comprise an input unit that allows the user to perform an input operation, and a trigger signal transmitting unit that transmits a trigger signal to the reference image holding unit and the movement vector integration unit in a case where information indicating that the trigger signal instructing to start a new operation is to be transmitted is input by the user via the input unit.

Alternatively, the ultrasound diagnostic apparatus may further comprise a trigger signal transmitting unit that performs image analysis with respect to the ultrasound images acquired sequentially and consecutively by the image acquisition unit to calculate an image change amount obtained from at least one of an image movement distance between two ultrasound images adjacent each other in time series or an image rotational amount between two ultrasound images adjacent each other in time series, and transmits a trigger signal instructing to start a new operation to the reference image holding unit and the movement vector integration unit in a case where the ultrasound images of which the image change amount is equal to or less than a predetermined threshold value are consecutively acquired by a predetermined number of frames.

A method of controlling an ultrasound diagnostic apparatus of the present invention is a method of controlling an ultrasound diagnostic apparatus that is used to compression-test an observation target in a subject by pressing the ultrasound probe against a body surface of the subject, the method comprising performing transmission of an ultrasound beam toward the subject to acquire ultrasound images sequentially and consecutively; holding the ultrasound image acquired in a state where a position of the ultrasound probe is fixed in order to depict a tomographic plane of the observation target as a reference image; calculating a movement vector indicating an image movement change between two ultrasound images that are consecutive for each predetermined number of frames among the sequentially acquired ultrasound images; integrating the movement vectors that are respectively calculated in the ultrasound images from a time when the reference image is held to a current time; generating a deformed image in which the ultrasound image of a current frame is moved and changed tracing back to a time when the reference image is held based on the integrated movement change; determining whether a tomographic plane of the subject depicted from the ultrasound image of the current frame and a tomographic plane of the subject depicted from the reference image are the same as each other by comparing the generated deformed image with the held reference image; and notifying a user of a determination result.

According to the present invention, an ultrasound diagnostic apparatus comprises an image acquisition unit that performs transmission of an ultrasound beam from the ultrasound probe toward the subject to acquire ultrasound images sequentially and consecutively; a display unit that displays the ultrasound image acquired by the image acquisition unit; a reference image holding unit that holds the ultrasound image acquired by the image acquisition unit in a state where a position of the ultrasound probe is fixed in order to depict a tomographic plane of the observation target on the display unit as a reference image; a movement vector calculation unit that calculates a movement vector indicating an image movement change between two ultrasound images that are consecutive for each predetermined number of frames among the ultrasound images sequentially acquired by the image acquisition unit; a movement vector integration unit that integrates the movement vectors that are respectively calculated by the movement vector calculation unit in the ultrasound images from a frame corresponding to the reference image held by the reference image holding unit to a current frame; a deformed image generation unit that generates a deformed image in which the ultrasound image of the current frame acquired by the image acquisition unit is moved and changed tracing back to a time when the reference image is held by the reference image holding unit based on a movement change integrated by the movement vector integration unit; a tomographic plane determination unit that determines whether a tomographic plane of the subject depicted from the ultrasound image of the current frame and a tomographic plane of the subject depicted from the reference image are the same as each other by comparing the deformed image generated by the deformed image generation unit with the reference image held by the reference image holding unit; and a determination result notification unit that notifies a user of a determination result obtained by the tomographic plane determination unit. Therefore, the user can perform an accurate diagnosis in the compression test.

DESCRIPTION OF THE PREFERRED EMBODIMENTS

Hereinafter, embodiments of the present invention will be described on the basis of the accompanying drawings.

Embodiment 1

Figure 1:
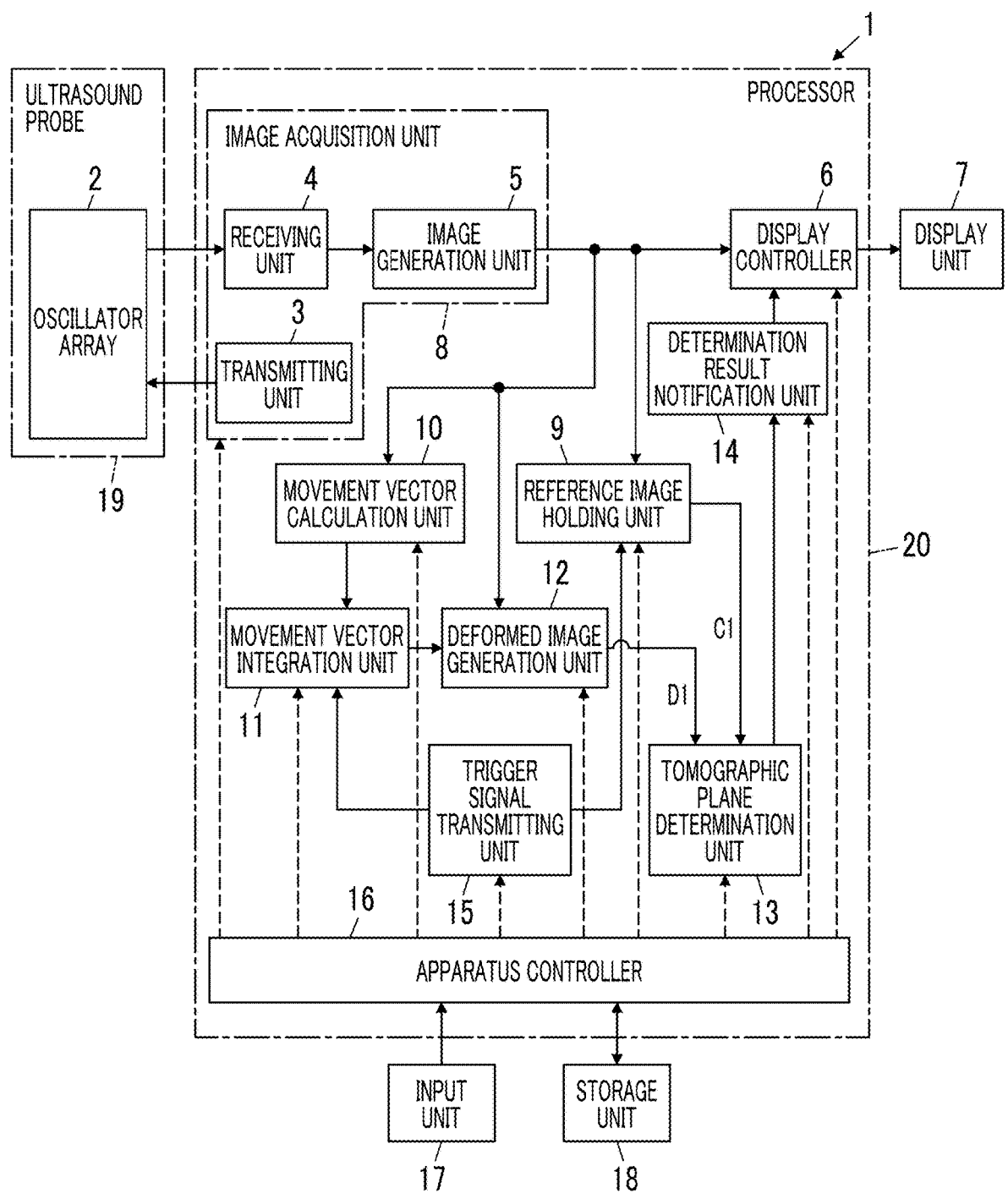
FIG. 1 is a block diagram illustrating a configuration of an ultrasound diagnostic apparatus according to Embodiment 1 of the present invention.

A configuration of an ultrasound diagnostic apparatus 1 according to Embodiment 1 of the present invention is illustrated in FIG. 1. As illustrated in FIG. 1, the ultrasound diagnostic apparatus 1 comprises an oscillator array 2, and a transmitting unit 3 and a receiving unit 4 that are connected to the oscillator array 2, respectively. An image generation unit 5, a display controller 6, and a display unit 7 are sequentially connected to the receiving unit 4. Here, an image acquisition unit 8 is configured by the transmitting unit 3, the receiving unit 4, and the image generation unit 5. Additionally, a reference image holding unit 9, a movement vector calculation unit 10, and a deformed image generation unit 12 are connected to the image generation unit 5. A movement vector integration unit 11 is connected to the movement vector calculation unit 10, and the deformed image generation unit 12 is connected to the movement vector integration unit 11. A tomographic plane determination unit 13 is connected to the reference image holding unit 9 and the deformed image generation unit 12. A determination result notification unit 14 is connected to the tomographic plane determination unit 13, and the display controller 6 is connected to the determination result notification unit 14. A trigger signal transmitting unit 15 is connected to the reference image holding unit 9 and the movement vector integration unit 11.

Moreover, an apparatus controller 16 is connected the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, and the trigger signal transmitting unit 15, and an input unit 17 and a storage unit 18 are connected to the apparatus controller 16. Here, the apparatus controller 16 and the storage unit 18 are connected to each other so as to be capable of transferring information bi-directionally.

Additionally, the oscillator array 2 is included in an ultrasound probe 19, and a processor 20 is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16.

The oscillator array 2 of the ultrasound probe 19 illustrated in FIG. 1 has a plurality of oscillators arranged in one dimension or two dimensions. These oscillators transmit ultrasonic waves in accordance with drive signals supplied from the transmitting unit 3, respectively, and receive ultrasonic echoes from the subject to output the received signals. The respective oscillators is configured by, for example, forming electrodes to both ends of piezoelectric material made of a piezoelectric ceramic represented by lead zirconate titanate (PZT), a polymeric piezoelectric element represented by polyvinylidene difluoride (PVDF), and a piezoelectric single crystal represented by a lead magnesium niobate-lead titanate solid solution (PMN-PT).

The transmitting unit 3 of the image acquisition unit 8 includes, for example, a plurality of pulse generators, and adjust the amounts of delay of the respective drive signals to supply the adjusted drive signals to the plurality of oscillators such that the ultrasonic waves transmitted from the plurality of oscillators of the oscillator array 2 form an ultrasound beam, based on a transmission delay pattern selected in accordance with the control signals from the apparatus controller 16. In this way, in a case where a pulsed or consecutive wave-like voltage is applied to electrodes of the plurality of oscillators of the oscillator array 2, the piezoelectric material expands and contracts, a pulsed or consecutive wave-like ultrasonic wave is generated from the respective oscillators, and the ultrasound beam is formed from a synthetic wave of the ultrasonic waves.

The transmitted ultrasound beam is reflected in, for example, targets such as a part of the subject and is propagated toward the oscillator array 2 of the ultrasound probe 19. The ultrasonic echoes propagated toward the oscillator array 2 in this way are received by the respective oscillators that constitute the oscillator array 2. In this case, the respective oscillators that constitute the oscillator array 2 expand and contract by receiving the propagated ultrasonic echoes, to generate electrical signals, and output the electrical signals to the receiving unit 4.

Figure 2:
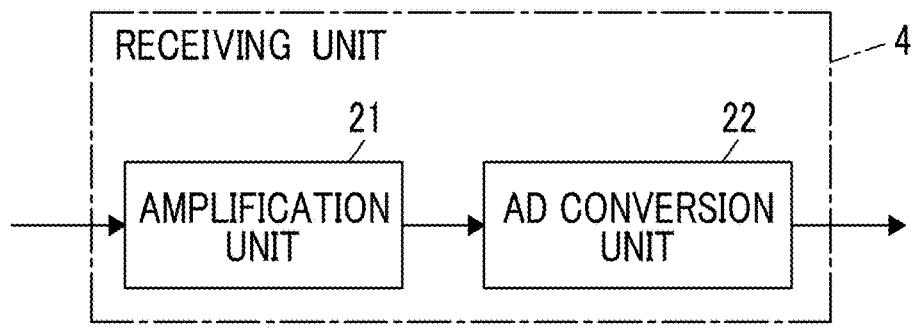
FIG. 2 is a block diagram illustrating an internal configuration of a receiving unit according to Embodiment 1 of the present invention.

The receiving unit 4 of the image acquisition unit 8 processes the received signals output from the oscillator array 2 in accordance with the control signals from the apparatus controller 16. As illustrated in FIG. 2, the receiving unit 4 has a configuration that an amplification unit 21 and an analog-digital (AD) conversion unit 22 are serially connected. The amplification unit 21 amplifies the received signals input from the respective oscillators that constitute the oscillator array 2, and transmits the amplified received signals to the AD conversion unit 22. The AD conversion unit 22 converts the received signals transmitted from the amplification unit 21 into digitalized data, and sends the data to the image generation unit 5 of the image acquisition unit 8.

Figure 3:
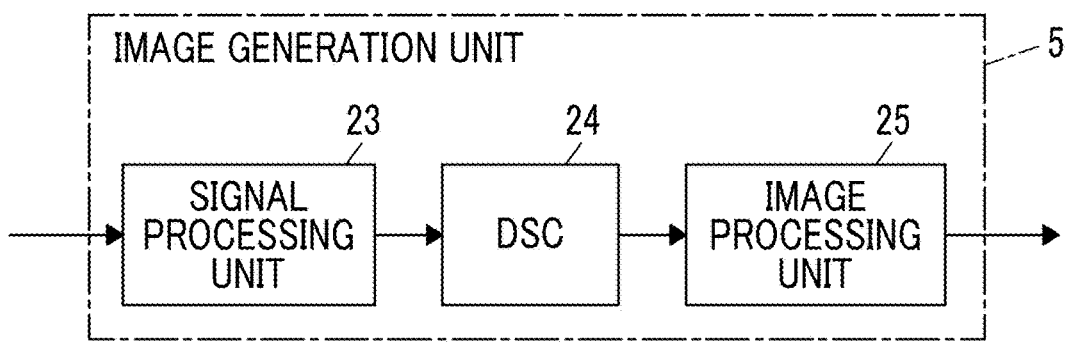
FIG. 3 is a block diagram illustrating an internal configuration of an image generation unit according to Embodiment 1 of the present invention.

As illustrated in FIG. 3, the image generation unit 5 of the image acquisition unit 8 has a configuration that a signal processing unit 23, a digital scan converter (DSC) 24, and an image processing unit 25 are serially connected. The signal processing unit 23 performs reception focus processing that addition (phasing addition) is performed by giving each delay to each data of the received signals, based on a reception delay pattern selected in accordance with the control signals from the apparatus controller 16. With the reception focus processing, sound ray signals in which focal points of the ultrasonic echoes are narrowed to one scan line are generated. Additionally, the signal processing unit 23 subjects the generated sound ray signals to the correction of damping resulting from a propagation distance depending on the depth at a position where the ultrasonic waves are reflected, and then performs envelope detection processing to generate B-mode image signals indicating a tissue within the subject. The B-mode image signals generated in this way are output to the DSC 24.

The DSC 24 of the image generation unit 5 raster-converts the B-mode image signals into image signals based on a scan mode of normal television signals to generate the ultrasound image. The image processing unit 25 of the image generation unit 5 subjects the image data obtained in the DSC 24 to various kinds of required image processing such as brightness correction, grayscale correction, sharpness correction, and color correction, and then outputs an ultrasound image to the display controller 6, the reference image holding unit 9, the movement vector calculation unit 10, and the tomographic plane determination unit 13.

Generally, DVT is known as a disease that a thrombus occurs in a deep vein. Although a normal deep vein in which the thrombus does not occur is easily deformed by compression, the deep vein in which the thrombus has occurred is not easily deformed due to the compression. Therefore, as a test for discovering the DVT, for example, a so-called compression test for observing a cross section of the compressed deep vein while compressing the deep vein having a concern that the DVT may occur is performed. The cross section of the deep vein represents the section of the deep vein in a case where the deep vein is cut across a central axis of the deep vein. Additionally, usually, the compression test is performed by observing the acquired ultrasound image while pressing the ultrasound probe 19 against the body surface of the subject to compress observation targets, such as the deep vein.

Figure 4:
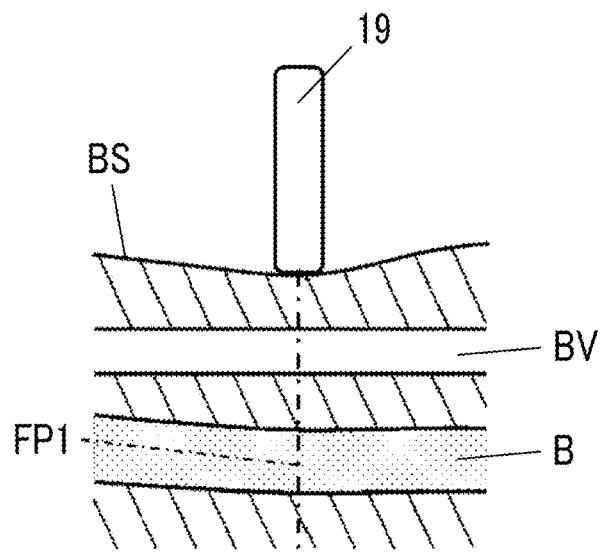
FIG. 4 is a schematic cross sectional view of a subject in a state where an ultrasound probe is in contact with a body surface.

As illustrated in FIG. 4, in a case where the compression test is performed, the reference image holding unit 9 of the processor 20 holds, as a reference image C1, the ultrasound image acquired by the image acquisition unit 8 in a state where the position of the ultrasound probe 19 is fixed and the observation target is not yet compressed by the ultrasound probe 19 in order to depict a tomographic plane of an observation target such as a blood vessel on the display unit 7. In an example illustrated in FIG. 4, since the ultrasound probe 19 is in contact with a body surface BS of the subject but is not strongly pressed, the tissue of the subject is not compressed, and a blood vessel BV, a bone B, and the like that are present in a subcutaneous part are in a state where they are not deformed and moved accompanying the compression. In this way, the reference image C1 represents, in the compression test, a tomographic plane FP1 of the subject in a state where the ultrasound probe 19 is positioned and the tissue of the subject is not compressed.

Although the tissue of the subject is deformed and moved by the ultrasound probe 19 being pressed against the body surface BS of the subject in the compression test, the movement vector calculation unit 10 of the processor 20 calculates the movement change of the ultrasound image in order to measure such deformation and movement of the tissue of the subject. More specifically, the movement vector calculation unit 10 calculates a movement vector indicating the image movement change between two consecutive ultrasound images for each frame among the ultrasound images sequentially acquired by the image acquisition unit 8. For example, the movement vector calculation unit 10 can calculate respective movement changes of respective pixels, that is, all the pixels in the ultrasound image as the movement vector by performing image analysis, such as so-called matching processing, for two consecutive ultrasound images.

The movement vector integration unit 11 of the processor 20 integrates the movement vectors that are respectively calculated by the movement vector calculation unit 10 in the ultrasound images from a time when the reference image is held by the reference image holding unit 9 to a current time, that is, from the ultrasound image held as the reference image C1 to the ultrasound image of the current frame. For example, in a case where the movement vector is calculated by the movement vector calculation unit 10 for each frame with respect to the ultrasound images of N frames from the time when the reference image C1 is held by the reference image holding unit 9 to the current time, the movement vector integration unit 11 calculates an integration vector indicating how much a pixel in an ultrasound image is moved and changed as an integrated movement change from the ultrasound image held as the reference image to the ultrasound image of an N-th frame, that is, a current frame S. In this case, the movement vector integration unit 11 holds, for example, an integration vector indicating an integrated movement change from a first frame to an N−1th frame, and can calculate the integration vector from the first frame to the N-th frame by adding the movement vector indicating the movement change between the ultrasound image of the N−1th frame and the ultrasound image of the N-th frame, and the held integration vector.

The deformed image generation unit 12 of the processor 20 generates a deformed image D1 in which the ultrasound image of the current frame acquired by the image acquisition unit 8 is moved and changed tracing back to a time when the reference image C1 is held by the reference image holding unit 9 based on a movement change integrated by the movement vector integration unit 11. Here, the meaning of "the ultrasound image of the current frame is moved and changed tracing back to a time when the reference image C1 is held" is the same as that the ultrasound image of the current frame is deformed by tracing retroactively the movement vectors calculated from the time when the reference image C1 is held to the current time. In this case, the deformed image generation unit 12 generates the deformed image D1 by moving all the pixels in the ultrasound image held as the reference image C1 tracing back to the integrated movement change, that is, by moving all the pixels in accordance with a vector in which a direction of the integration vector calculated by the movement vector integration unit 11 is reversed.

As illustrated in FIG. 1, the tomographic plane determination unit 13 of the processor 20 determines whether the tomographic plane of the subject depicted from the ultrasound image of the current frame and the tomographic plane of the subject depicted from the reference image C1 are the same as each other, by comparing the deformed image D1 generated by the deformed image generation unit 12 with the reference image C1 held by the reference image holding unit 9. In this case, by performing image analysis on the deformed image D1 and the reference image C1, the tomographic plane determination unit 13 calculates a similarity between these two images, and performs determination based on the calculated similarity. For example, the tomographic plane determination unit 13 can determine that in a case where the calculated similarity is equal to or more than a threshold value, the tomographic plane of the subject depicted from the reference image C1 and the tomographic plane of the subject depicted from the ultrasound image of the current frame are the same as each other, and can determine that in a case where the calculated similarity is less than the threshold value, the tomographic plane of the subject depicted from the ultrasound image of the current frame and the tomographic plane of the subject depicted from the reference image C1 are different from each other.

Figure 5:
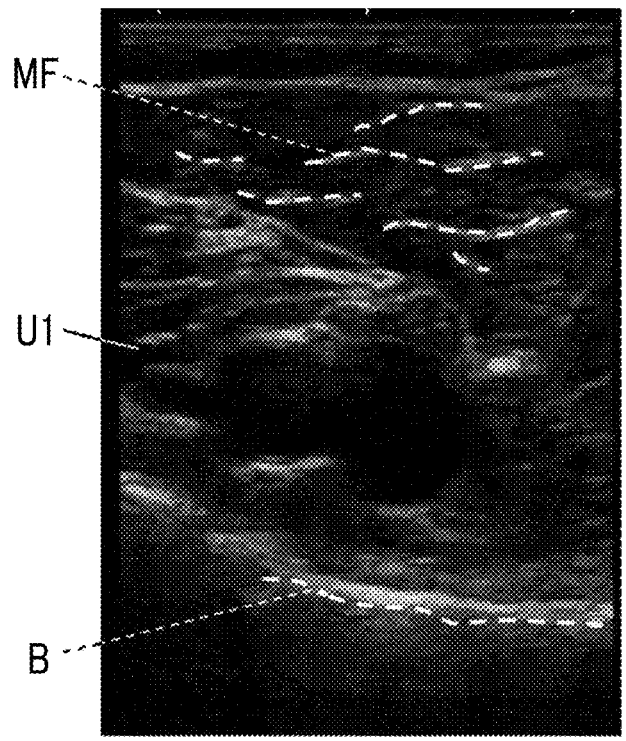
FIG. 5 is an ultrasound image illustrating a tomographic plane of the subject in a state of not being pressed by the ultrasound probe.
Figure 6:
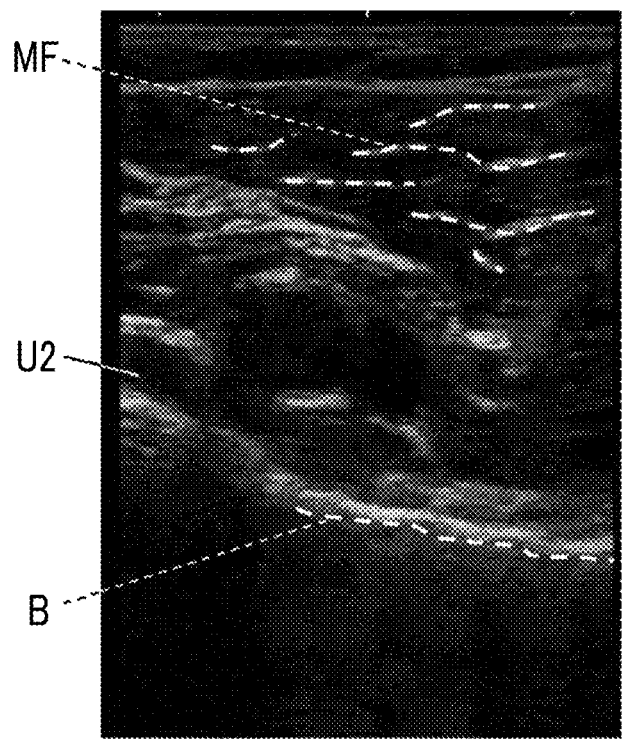
FIG. 6 is an ultrasound image illustrating the tomographic plane of the subject in a state of being pressed by the ultrasound probe.

Here, in a case where the tomographic plane FP1 of the subject depicted from the ultrasound image of the current frame is the same as the tomographic plane FP1 of the subject depicted from the reference image C1, for example, as illustrated in FIGS. 5 and 6, a difference between the ultrasound image of the current frame and the reference image C1 greatly originates in the image movement change caused by the ultrasound probe 19 being pressed against the body surface BS of the subject. Therefore, in this case, the similarity between the reference image C1 and the deformed image is high. Here, FIG. 5 illustrates an ultrasound image U1 which corresponds to the reference image C1 and in which the tissue of the subject is not compressed by the ultrasound probe 19, FIG. 6 illustrates an ultrasound image U2 in which the tissue of the subject is compressed by the ultrasound probe 19. The tomographic plane of the subject depicted from the ultrasound image U1 and the tomographic plane of the subject depicted from the ultrasound image U2 are the same as each other. Comparing FIG. 5 with FIG. 6, it can be seen that, as the tissue of the subject is compressed by the ultrasound probe 19, muscle fibers MF are deformed and the bone B moves above the image.

Figure 7:
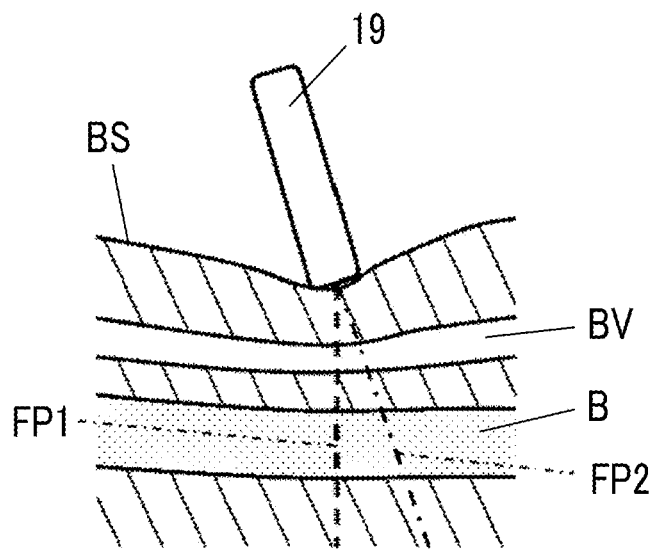
FIG. 7 is a schematic cross sectional view of the subject pressed by the ultrasound probe.
Figure 8:
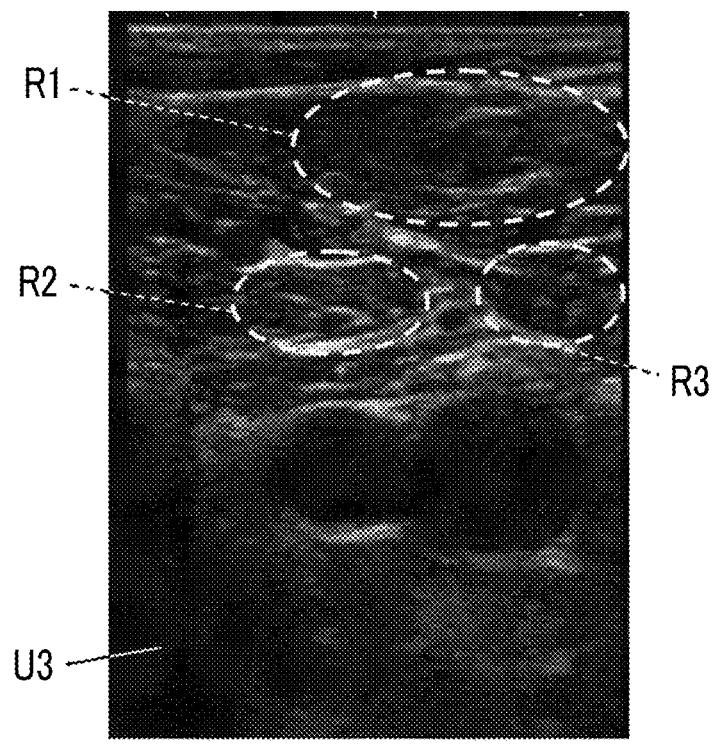
FIG. 8 is an ultrasound image illustrating the tomographic plane of the subject depicted from a reference image.
Figure 9:
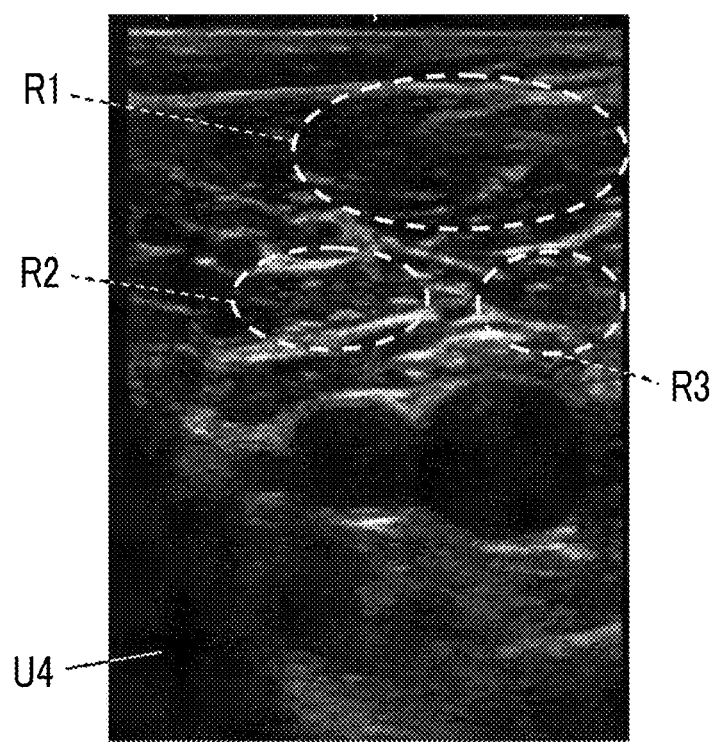
FIG. 9 is an ultrasound image illustrating a tomographic plane different from the tomographic plane of the subject depicted from the reference image.

On the other hand, as illustrated in FIG. 7, in a case where the ultrasound probe 19 inclines in a case where the ultrasound probe 19 is pressed against the body surface BS of the subject, and the tomographic plane FP2 of the subject depicted from the ultrasound image of the current frame is greatly different from the tomographic plane FP1 of the subject depicted from the reference image C1, for example, as illustrated in FIGS. 8 and 9, the difference between the ultrasound image of the current frame and the reference image C1 cannot be indicated only by the simple movement change of the image. Therefore, in this case, the similarity between the reference image C1 and the deformed image is low. FIG. 8 illustrates an ultrasound image U3 from which the same tomographic plane as the tomographic plane FP1 of the subject depicted from the reference image C1 is depicted, and FIG. 9 illustrates an ultrasound image U4 from which the tomographic plane FP2 inclined from the tomographic plane FP1 is depicted. As illustrated in FIGS. 8 and 9, structure patterns of muscle fibers indicated by pixels with high luminance are included in regions R1, R2, and R3 that are respectively surrounded by broken lines in the ultrasound image U3 and the ultrasound image U4. Because the structure patterns of the muscle fibers in the regions R1, R2, and R3 in the ultrasound image U3 are different from the structure patterns of the muscle fibers in the regions R1, R2, and R3 in the ultrasound image U4, it can be seen that the structure patterns thereof cannot be indicated by the simple movement change of the image.

In this way, it can be seen that it can be determined whether the tomographic plane of the subject depicted from the ultrasound image of the current frame and the tomographic plane of the subject depicted from the reference image C1 are the same as each other, based on the similarity between the deformed image D1 and the reference image C1.

Additionally, the tomographic plane determination unit 13 calculates the similarity between the deformed image D1 and the reference image C1 of by performing the image analysis on the deformed image D1 and the reference image C1. However, more specifically, for example, the tomographic plane determination unit 13 can calculate the similarity by performing so-called matching between frames on the deformed image D1 and the reference image C1. Additionally, for example, a machine learning technique described in Csurka et al.: Visual Categorization with Bags of Keypoints, Proc. of ECCV Workshop on Statistical Learning in Computer Vision, pp. 59-74 (2004), a general image recognition technique using deep learning described in Krizhevsky et al.: Image Net Classification with Deep Convolutional Neural Networks, Advances in Neural Information Processing Systems 25, and pp. 1106-1114 (2012), or the like can be used for the calculation of the similarity in addition to the simple matching.

The determination result notification unit 14 of the processor 20 notifies a user of the determination result obtained by the tomographic plane determination unit 13. Although not illustrated, the determination result notification unit 14 can notify the user of the determination result by, for example, displaying, on the display unit 7, texts, images, or the like indicating that the tomographic plane of the subject depicted from the ultrasound image of the current frame is the same as or different from the tomographic plane of the subject depicted from the reference image C1, as the determination result. Additionally, although not illustrated, for example, a voice generation unit that generates voice may also be provided in the ultrasound diagnostic apparatus 1, and the determination result notification unit 14 can also notify the user of the determination result via the voice caused by the voice generation unit. In this way, since the determination result notification unit 14 notifies the user of the determination result automatically obtained by the tomographic plane determination unit 13, the user can grasp easily whether the tomographic plane of the subject being depicted currently is a tomographic plane that the user has intended.

The trigger signal transmitting unit 15 of the processor 20 transmits trigger signals indicating that operation is newly started with respect to the reference image holding unit 9 and the movement vector integration unit 11 by the operation of the user via the input unit 17. In a case where the reference image holding unit 9 has received the trigger signals from the trigger signal transmitting unit 15, the reference image holding unit 9 overwrites an ultrasound image newly acquired by the image acquisition unit 8 on the ultrasound image already held as the reference image C1, and holds the overwritten ultrasound image as a new reference image C1. Additionally, in a case where the movement vector integration unit 11 has received the trigger signals, the movement vector integration unit 11 eliminates the image movement change that has already been integrated, and starts integration of a movement vector newly calculated by the movement vector calculation unit 10.

The apparatus controller 16 of the processor 20 performs control of the respective units of the ultrasound diagnostic apparatus 1 based on the programs that are stored in advance in the storage unit 18 and the like and the operation of the user via the input unit 17.

Under the control of the apparatus controller 16, the display controller 6 of the processor 20 performs predetermined processing on an ultrasound image generated by the image generation unit 5 of the image acquisition unit 8, and displays the ultrasound image on the display unit 7.

The display unit 7 of the ultrasound diagnostic apparatus 1 displays the ultrasound image and the like under the control of the display controller 6, and includes display units such as a liquid crystal display (LCD), and an organic electroluminescence (EL) display.

The input unit 17 of the ultrasound diagnostic apparatus 1 is for the user to perform input operation, and can be configured to comprise a keyboard, a mouse, a trackball, a touchpad, a touch panel, and the like.

The storage unit 18 stores operating programs and the like of the ultrasound diagnostic apparatus 1. As the storage unit 18, storage media such as a hard disc drive (HDD), a solid state drive (SSD), a flexible disc (FD), a magneto-optical (MO) disc, a magnetic tape (MT), a random access memory (RAM), a compact disc (CD), a digital versatile disc (DVD), a secure digital (SD) card, a universal serial bus (USB) memory or the like, or a server can be used.

In addition, the processor 20 having the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16 is configured from a central processing unit (CPU) and control programs for making the CPU perform various kinds of processing. However, the processor 20 may be configured from a field programmable gate array (FPGA), a digital signal processor (DSP), an application specific integrated circuit (ASIC), or other integrated circuits (ICs), or may be configured by combining them.

Also, the processor 20 can be configured by partially or entirely integrating the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16 of the processor 20 into one CPU.

Figure 10:
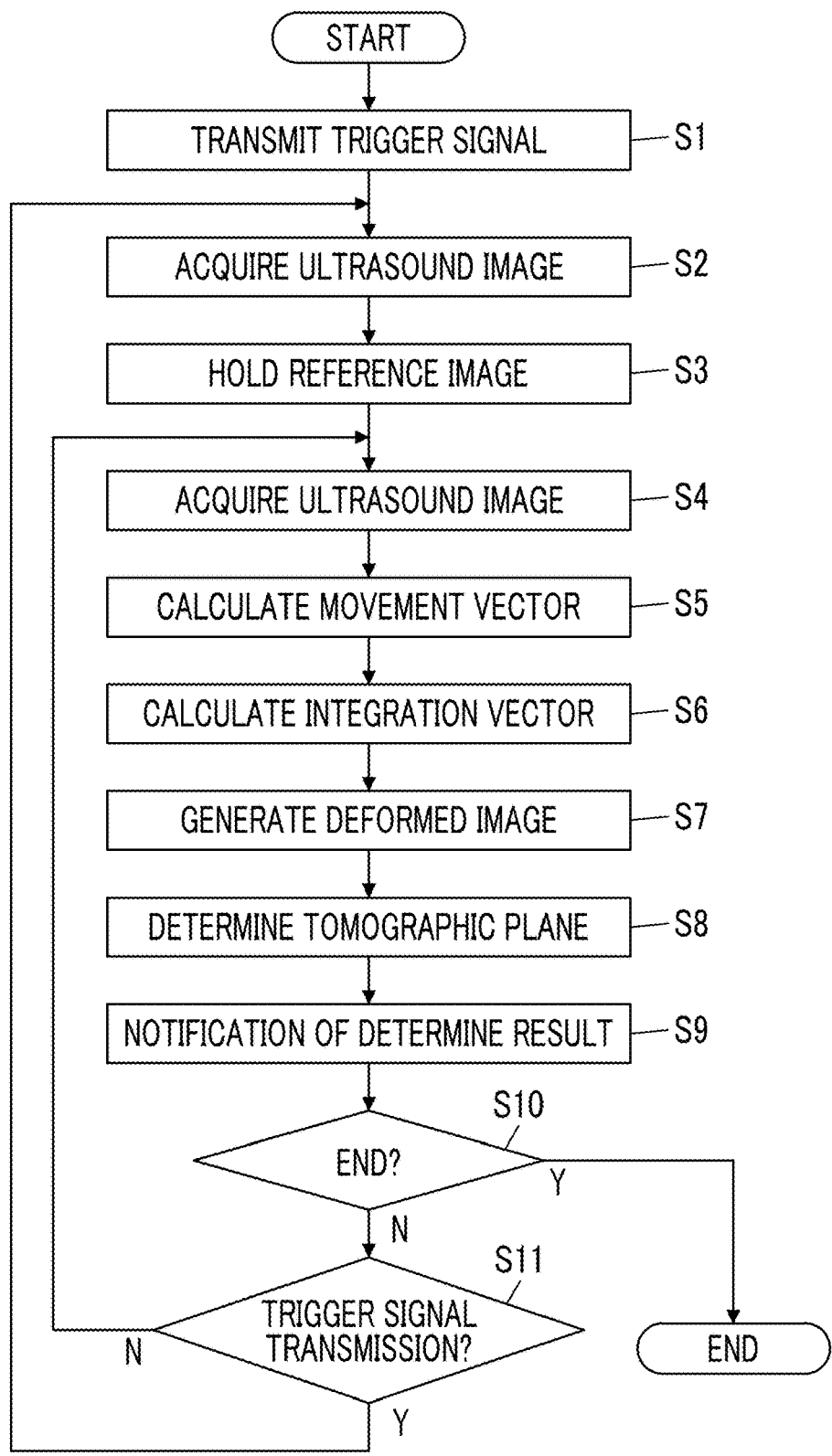
FIG. 10 is a flowchart illustrating an operation of the ultrasound diagnostic apparatus according to Embodiment 1 of the present invention.

Next, the operation of the ultrasound diagnostic apparatus 1 in Embodiment 1 will be described in detail using a flowchart illustrated in FIG. 10. The flowchart illustrated in FIG. 10 illustrates the operation of the ultrasound diagnostic apparatus 1 in a case where the compression test to the subject is performed.

First, in Step S1, a user fixes the position of the ultrasound probe 19 in order to depict the tomographic plane of the observation target, such as the blood vessel BV, for example, as illustrated in FIG. 4. Moreover, in a case where information indicating that the trigger signal is to be transmitted is input by the user via the input unit 17, the trigger signal transmitting unit 15 transmits the trigger signal to the reference image holding unit 9 and the movement vector integration unit 11.

Next, in Step S2, the ultrasound beam is transmitted toward the subject from the oscillator array 2 of the ultrasound probe 19, and the received signals are generated by the oscillator array 2 based on ultrasonic echoes propagated toward the oscillator array 2 from the subject. As the received signals generated in this way are sequentially processed by the receiving unit 4 and the image generation unit 5 of the image acquisition unit 8, the ultrasound image representing the tomographic plane of the subject is acquired.

In Step S3, the reference image holding unit 9 holds the ultrasound image acquired in Step S2 as the reference image C1.

In Step S4, the image acquisition unit 8 acquires the ultrasound image in the same manner as Step S2.

In Step S5, the movement vector calculation unit 10 calculates the movement vector indicating the image movement change between two consecutive ultrasound images, that is, two ultrasound images acquired in Step S2 and Step S4. Hereinafter, it is assumed that the movement vector calculation unit 10 calculates movement changes of all the pixels in two ultrasound images as the movement vectors, respectively, for description.

In Step S6, the movement vector integration unit 11 integrates the movement vector calculated in Step S5. The movement vector integration unit 11 performs, for example, integration of the movement vector for each of all the pixels of the ultrasound images. At the current time, since the movement vector calculated in Step S5 is only one per each pixel, an integration result, that is, an integration vector, obtained in Step S6 is equal to the movement vector calculated in Step S5. Also, the movement vector integration unit 11 holds the newest integration vector obtained in Step S6.

In Step S7, the deformed image generation unit 12 generates the deformed image D1 in which the ultrasound image of the current frame acquired in Step S4 is moved and changed tracing back to the time when the reference image C1 is held in Step S3 based on the image movement change integrated in Step S6. The deformed image generation unit 12 generates the deformed image D1, for example, by moving all the pixels of the ultrasound image of the current frame tracing back the movement change integrated in Step S6.

In Step S8, the tomographic plane determination unit 13 determines whether the tomographic plane of the subject depicted from the reference image C1 and the tomographic plane of the subject depicted from the ultrasound image of the current frame are the same as each other, by comparing the reference image C1 held in Step S3 with the deformed image D1 generated in Step S7. The tomographic plane determination unit 13 can calculate the similarity between the reference image C1 and the deformed image D1 by, for example, performing matching between frames on the reference image C1 and the deformed image D1, and can perform the determination based on the calculated similarity.

In Step S9, the determination result notification unit 14 notifies the user of the determination result obtained in Step S8. For example, the determination result notification unit 14 can notify the user of the determination result by displaying texts, images, or the like indicating the determination result superimposed on the ultrasound image of the current frame.

In Step S10, whether to end the operation of the ultrasound diagnostic apparatus 1 is determined. For example, although not illustrated, it is determined that the operation of the ultrasound diagnostic apparatus 1 is to be ended in a case where an end button for ending the operation of the ultrasound diagnostic apparatus 1 is displayed on the display unit 7, and the end button is pushed by the user via the input unit 17, and it is determined that the operation of the ultrasound diagnostic apparatus 1 is not ended in a case where the end button is not pushed. In a case where it is determined that the operation of the ultrasound diagnostic apparatus 1 is not ended in Step S10, the process proceeds to Step S11.

In the following Step S11, it is determined whether the trigger signal is newly transmitted by the trigger signal transmitting unit 15. In this case, in a case where the information indicating that the trigger signal is to be transmitted is not newly input by the user via the input unit 17 and the trigger signal is not newly transmitted by the trigger signal transmitting unit 15, it is determined that the trigger signal is not newly transmitted, and the process returns to Step S4.

In Step S4, the ultrasound image is newly acquired by the image acquisition unit 8.

In the following Step S5, the movement vector calculation unit 10 calculates the movement vector based on two ultrasound images acquired in the current Step S4 and the previous Step S4.

In Step S6, the movement vector integration unit 11 calculates the integrated movement change from the time when the reference image C1 is held in Step S3 to the current time. In this case, the movement vector integration unit 11 calculates a new integration vector by adding the newest integration vector that is held to the movement vector newly obtained in Step S5. Since the newest integration vector held at the current time is equal to the movement vector calculated from the ultrasound image of a first frame and the ultrasound image of a second frame, the movement vector integration unit 11 adds the movement vector calculated from the ultrasound image of the first frame and the ultrasound image of the second frame to the movement vector newly obtained in Step S5, in all the pixels of the ultrasound image. Additionally, the movement vector integration unit 11 holds the new integration vector calculated in Step S6 instead of the integration vector already held.

In Step S7, the deformed image generation unit 12 deforms the ultrasound image of the current frame generated in Step S4 to newly generate the deformed image D1 based on the movement change of each pixel newly integrated in Step S6.

In Step S8, the tomographic plane determination unit 13 determines whether the tomographic plane of the subject depicted from the ultrasound image held as the reference image C1 and the tomographic plane of the subject depicted from the ultrasound image of the current frame are the same as each other, by comparing the reference image C1 held in Step S3 with the deformed image D1 newly generated in Step S7.

In Step S9, the determination result notification unit 14 notifies the user of the determination result newly obtained in Step S8.

In the following Step S10, it is determined whether the operation of the ultrasound diagnostic apparatus 1 is to be ended. In a case where it is determined that the operation of the ultrasound diagnostic apparatus 1 is not ended in Step S10, the process proceeds to Step S11.

In Step S11, it is determined whether the trigger signal is newly transmitted by the trigger signal transmitting unit 15.

In this way, the processing in Step S4 to Step S11 is repeated until it is determined that the operation of the ultrasound diagnostic apparatus 1 is to be ended in Step S10 or it is determined that the trigger signal is newly transmitted by the trigger signal transmitting unit 15 in Step S11. In this case, in Step S6, the movement vector integration unit 11 calculates a new integration vector by adding the newest integration vector that is held to the movement vector newly calculated in Step S5. Moreover, the movement vector integration unit 11 holds the newly calculated integration vector instead of the integration vector held until now. Whenever Step S4 to Step S11 are repeated in this way, the new deformed image D1 is generated in Step S7, and the determination in Step S8 is performed based on the generated new deformed image D1 and the reference image C1, and the user is notified of the determination result in Step S9.

Also, in Step S11, in a case where the information indicating that the trigger signal is to be newly transmitted is input by the user via the input unit 17 and the trigger signal is transmitted by the trigger signal transmitting unit 15, it is determined that the trigger signal is newly transmitted, and the process returns to Step S2. In this case, the user fixes the position of the ultrasound probe 19 in a state where the ultrasound probe 19 does not compress the subject, for example, as illustrated in FIG. 4. In this way, in a case where the trigger signal is newly transmitted to the reference image holding unit 9 and the movement vector integration unit 11 by the trigger signal transmitting unit 15, the reference image holding unit 9 eliminates the reference image C1 held until now, and the movement vector integration unit 11 eliminates the held integration vector.

In Step S2, the image acquisition unit 8 newly acquires the ultrasound image. In the following Step S3, the reference image holding unit 9 holds the ultrasound image newly acquired in Step S2 as the reference image C1.

In Step S4, the image acquisition unit 8 newly acquires an ultrasound image in the same manner as Step S2.

In Step S5, the movement vector calculation unit 10 calculates the movement vector indicating the image movement change of the image between two ultrasound images acquired in Step S2 and Step S4.

In Step S6, the movement vector integration unit 11 integrates the movement vector calculated in Step S5. Here, since the trigger signal is transmitted to the movement vector integration unit 11 by the trigger signal transmitting unit 15 in Step S11, the integration vector held by the movement vector integration unit 11 is eliminated. For that reason, the current integration vector obtained by the movement vector integration unit 11 is equal to the movement vector calculated in Step S5.

In Step S7, the deformed image generation unit 12 generates the deformed image D1 by deforming the ultrasound image of the current frame acquired by Step S4 based on the integrated movement change in Step S6.

In Step S8, the tomographic plane determination unit 13 determines whether the tomographic plane of the subject depicted from the reference image C1 newly held in Step S3 and the tomographic plane of the subject depicted from the ultrasound image of the current frame are the same as each other, by comparing the deformed image D1 generated in Step S7 with the reference image C1 newly held in Step S3. In Step S9, the determination result notification unit 14 notifies the user of the determination result obtained in Step S8.

In the following Step S10, it is determined whether the operation of the ultrasound diagnostic apparatus 1 is to be ended. In a case where it is determined that the operation of the ultrasound diagnostic apparatus 1 is not ended in Step S10, the process proceeds to Step S11. Also, in a case where it is determined that the operation of the ultrasound diagnostic apparatus 1 is to be ended in Step S10, the operation of the ultrasound diagnostic apparatus 1 is ended.

As described above, with the ultrasound diagnostic apparatus 1 according to Embodiment 1 of the present invention, the deformed image generation unit 12 generates the deformed image D1 in which the ultrasound image of the current frame is moved and changed retroactively based on the integrated movement change from the time when the reference image C1 is held by the reference image holding unit 9 to the current time, the tomographic plane determination unit 13 performs determination of the tomographic plane by comparing the deformed image D1 with the reference image C1, the determination result notification unit 14 notifies the user of the determination result. Thus, the user can easily grasp whether the tomographic plane of the subject currently being depicted on the display unit 7 is an intended tomographic plane, and can perform the accurate diagnosis.

In Embodiment 1, the tomographic plane determination unit 13 determines that the tomographic plane of the subject depicted from the reference image C1 and the tomographic plane of the subject depicted from the ultrasound image of the current frame are the same each other in a case where the similarity between the deformed image D1 and the reference image C1 is equal to or more than the threshold value, and determines that the tomographic plane of the subject depicted from the reference image C1 and the tomographic plane of the subject depicted from the ultrasound image of the current frame are different from each other in a case where the similarity is less than the threshold value. However, the determination method of the tomographic plane determination unit 13 is not particularly limited thereto.

For example, the tomographic plane determination unit 13 can also divide the criteria for the determination of the similarity into a plurality of levels, and can determine the tomographic plane depending on which level the calculated similarity belongs to. For example, the tomographic plane determination unit 13 can determine that two of the tomographic plane of the subject depicted from the reference image C1 and the tomographic plane of the subject depicted from the ultrasound image of the current frame are the same as each other in a case where the calculated similarity is equal to or more than a first threshold value. The tomographic plane determination unit 13 can determine that there is high possibility that two tomographic planes are the same as each other in a case where the calculated similarity is less than the first threshold value and is equal to or more than a second threshold value. The tomographic plane determination unit 13 can determine that two tomographic planes are different from each other in a case where the calculated similarity is less than the second threshold value.

In this case, for example, the determination result notification unit 14 can display texts, images, or the like indicating the determination result according to the levels of determination obtained by the tomographic plane determination unit 13 superimposed on the ultrasound image of the current frame. Additionally, for example, the determination result notification unit 14 can also apply colors according to the levels of similarity to the ultrasound image of the current frame to display the colors on the display unit 7. Additionally, the determination result notification unit 14 can also display the value of the similarity calculated by the tomographic plane determination unit 13 superimposed on the ultrasound image of the current frame.

In this way, since the tomographic plane determination unit 13 determines the tomographic planes depending on the levels of similarity and the determination result notification unit 14 notifies the user of the determination result, the user can perform more accurate diagnosis by checking the determination result.

Additionally, the movement vector calculation unit 10 can interpolate the movement vector of each pixel in the ultrasound image, using a plurality of calculated movement vectors. More specifically, for example, the movement vector calculation unit 10 can calculate the movement vector by performing the image analysis with respect to all the pixels in the ultrasound image, and can interpolate the movement vector of each pixel by weight-averaging a plurality of movement vectors calculated for each pixel and pixels located therearound. Accordingly, the movement vector calculation unit 10 can calculate a more accurate movement vector.

Additionally, in this case, since the movement vector integration unit 11 calculates the integration vector using the movement vector interpolated by the movement vector calculation unit 10, the movement vector integration unit 11 can calculate a more accurate integration vector.

Additionally, in Embodiment 1, although the movement vector calculation unit 10 calculates the movement vectors for all the pixels in the ultrasound image, respectively, the calculation method of the movement vectors is not particularly limited thereto. For example, the movement vector calculation unit 10 can calculate the movement change of the high-luminance pixel of which the luminance is equal to or more than a predetermined threshold value, among all the pixels in the ultrasound image, as the movement vector. In this case, the movement vector integration unit 11 integrates the movement vector for each high-luminance pixel in the ultrasound image, and the deformed image generation unit 12 generates the deformed image D1 based on the movement change of each high-luminance pixel in the reference image C1.

Accordingly, since the number of pixels to be handled by the movement vector calculation unit 10, the movement vector integration unit 11, and the deformed image generation unit 12 can be reduced, the calculation load in the ultrasound diagnostic apparatus 1 can be mitigated.

Additionally, in this case, the deformed image generation unit 12 can generate the deformed image D1 by dividing the ultrasound image into a plurality of regions each including at least one high-luminance pixel, and moving the plurality of regions, respectively, based on the movement change integrated for each of the high-luminance pixels by the movement vector integration unit 11. Also, the tomographic plane determination unit 13 performs the determination of the tomographic plane for each of the plurality of regions divided by the deformed image generation unit 12.

In this case, the determination result obtained by the tomographic plane determination unit 13 corresponds to the divided plurality of regions at the time when the reference image C1 is held. Therefore, the deformed image generation unit 12 can move and change the divided plurality of regions to the current time according to the integration result obtained by the movement vector integration unit 11, the tomographic plane determination unit 13 can reflect the determination result to the plurality of regions in the ultrasound image of the current frame, and the determination result notification unit 14 can notify the user of the determination result of the tomographic plane for each of the plurality of regions in the ultrasound image of the current frame.

Accordingly, since the determination result notification unit 14 can notify the user of a more detailed determination result, the user can more accurately perform the determination whether the tomographic plane of the subject depicted from the ultrasound image of the current frame and the tomographic plane of the subject depicted from the reference image C1 are the same as each other.

Additionally, the movement vector calculation unit 10 can also perform the image analysis with respect to the ultrasound image to calculate the edge resemblance of the image, and can calculate the movement vector with respect to a pixel in which the calculated edge resemblance is equal to or more than a threshold value. Here, the edge resemblance of the image is an index indicating contour likelihood on the image, and is calculated using the contrast or the like between target pixels and surrounding pixels.

Additionally, for example, the movement vector calculation unit 10 can also partition the ultrasound image into a predetermined number of regions, and can calculate the movement change of one pixel in each region as the movement vector of each region. In this case, the movement vector integration unit 11 can integrate the movement vector for each of the regions partitioned by the movement vector calculation unit, and the deformed image generation unit 12 can generate the deformed image D1 based on the movement change of each region in the reference image C1.

Additionally, in this case, the tomographic plane determination unit 13 can calculate the similarity between the deformed image D1 and the reference image C1 for each of the regions partitioned by the movement vector calculation unit 10, and can perform the determination of the tomographic plane for each partitioned region based on the calculated similarity. Moreover, the determination result notification unit 14 can notify the user of the determination result for each of the partitioned plurality of regions. Also in this case, the deformed image generation unit 12 can move and change the divided plurality of regions to the current time, the tomographic plane determination unit 13 can reflect the determination result to the plurality of regions in the ultrasound image of the current frame, and the determination result notification unit 14 can notify the user of the determination result of the tomographic plane for each of the plurality of regions in the ultrasound image of the current frame.

Additionally, in Embodiment 1, the movement vector calculation unit 10 calculates the movement vector whenever the ultrasound image is sequentially and consecutively acquired by the image acquisition unit 8. However, the movement vector between two ultrasound images that are consecutive for each of predetermined frames can be calculated. Accordingly, since the number of movement vectors to be calculated by unit time by the movement vector calculation unit 10 can be reduced, the calculation load of the ultrasound diagnostic apparatus 1 can be mitigated.

Additionally, in Embodiment 1, the deformed image generation unit 12 generates the deformed image D1 immediately after a first integration vector is obtained by the movement vector integration unit 11. However, the deformation and the movement of the tissue of the subject are more reflected in the integration vector calculated by the movement vector integration unit 11 as the time during which the tissue of the subject is compressed by the ultrasound probe 19 elapses. Therefore, for example, generation of the deformed image D1 can be started from the time when the movement vector is integrated with respect to the ultrasound image of a given number of frames of 5 to 10 frames.

Embodiment 2

Figure 11:
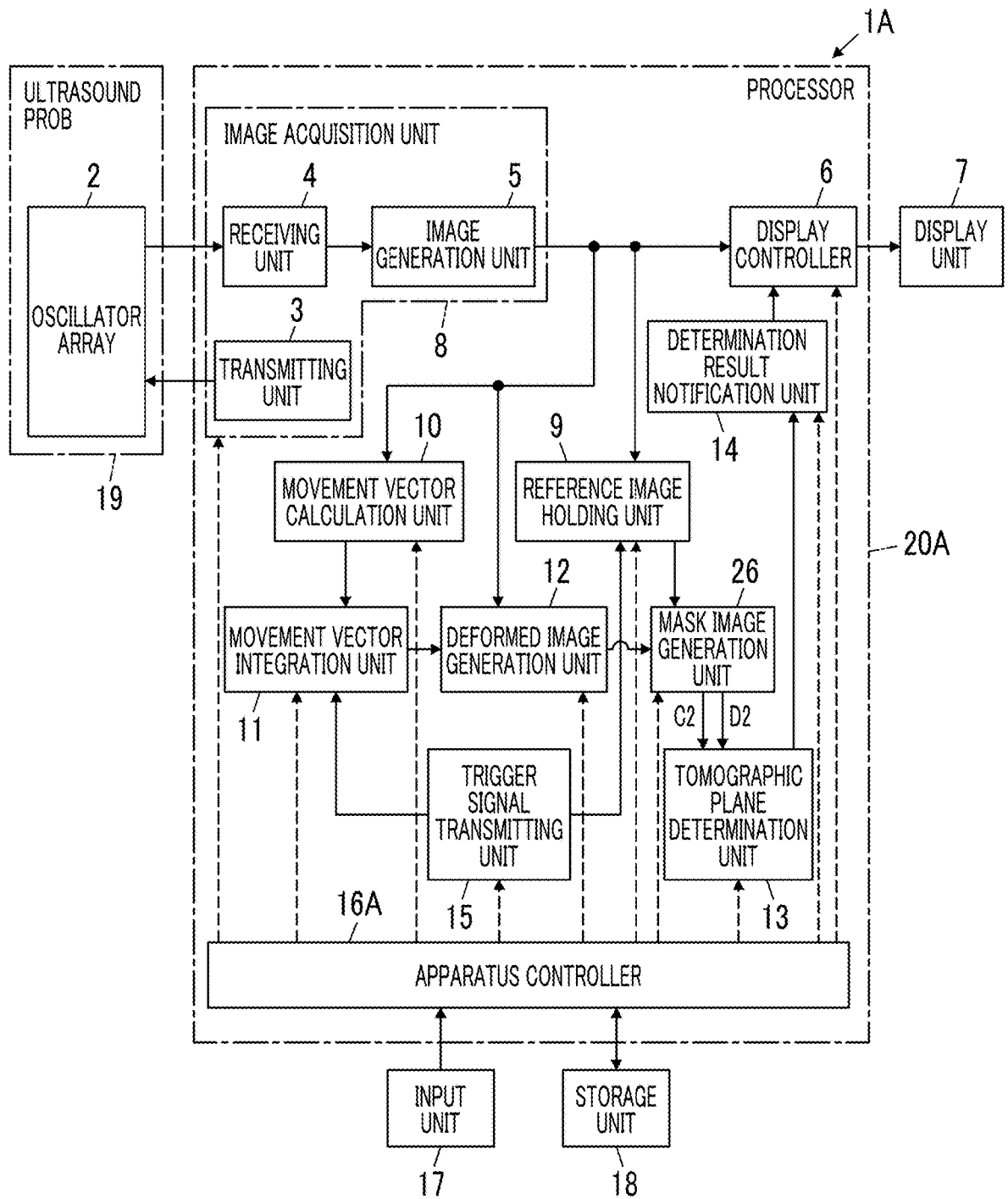
FIG. 11 is a block diagram illustrating a configuration of an ultrasound diagnostic apparatus according to Embodiment 2 of the present invention.

The configuration of an ultrasound diagnostic apparatus 1A according to Embodiment 2 of the present invention is illustrated in FIG. 11. The ultrasound diagnostic apparatus 1A of Embodiment 2 comprises an apparatus controller 16A instead of the apparatus controller 16 in the ultrasound diagnostic apparatus 1 of Embodiment 1 illustrated in FIG. 1, and further comprises a mask image generation unit 26.

In the ultrasound diagnostic apparatus 1A of Embodiment 2, the mask image generation unit 26 is connected to the reference image holding unit 9 and the deformed image generation unit 12, and the tomographic plane determination unit 13 is connected to the mask image generation unit 26. Additionally, the apparatus controller 16A is connected to the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the mask image generation unit 26. Additionally, the input unit 17 and the storage unit 18 are connected to the apparatus controller 16A. Here, the apparatus controller 16A and the storage unit 18 are connected to each other so as to be capable of transferring information bi-directionally.

Moreover, a processor 20A is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, the apparatus controller 16A, and the mask image generation unit 26.

Here, in a case where a test of the DVT is performed, blood vessels, muscle fibers, bones, nerves, tendons, and the like are often included in the ultrasound image. However, for example, as illustrated in FIG. 7, in a case where the tomographic plane depicted from the ultrasound image as the ultrasound probe 19 is inclined has changed from the tomographic plane FP1 to the tomographic plane FP2, the change in the structure pattern of the muscle fibers and the bones expressed by pixels with high luminance in the ultrasound image is particularly remarkable. Regarding the muscle fibers, as illustrated in FIGS. 8 and 9, it can be seen that, as the tomographic plane depicted from the ultrasound image shifts, the structure patterns of the muscle fibers in regions R1, R2, and R3 change. Additionally, although the bone is not illustrated, the structure of the section of the bone changes depending on a location, and the shape of the surface of the bone is not uniform. Therefore, in a case where the tomographic plane depicted from the ultrasound image shifts, the structure pattern of the bone changes. For that reason, the determination of the tomographic plane is more easily performed by comparing the deformed image with the ultrasound image of the current frame while paying attention to at least one of the muscle fibers or the bone.

The mask image generation unit 26 of the processor 20A performs the image analysis on the deformed image generated by the deformed image generation unit 12 and the ultrasound image held by the reference image holding unit 9 as the reference image, and detects at least one of the muscle fibers or the bone, and generates the mask image C2 in which the regions other than the muscle fibers and the bone detected with respect to the reference image are masked and the mask image D2 in which the regions other than the muscle fibers and the bone detected with respect to the deformed image are masked. Here, masking the regions other than the muscle fibers and the bone means covering regions other than the muscle fibers and the bone in the ultrasound image, and includes superimposing and painting away or shading an image for covering a target region. Additionally, in a case where the regions other than the muscle fibers and the bone are masked, as long as the target region is covered, for example, an image having transmittance such as a translucent image may be superimposed.

Here, generally, since the signal intensity of ultrasonic echoes from the surface of the bone is stronger than the signal intensity of the ultrasonic echoes from other than the bone, the mask image generation unit 26 can detect, for example, a region where the luminance in the ultrasound image is equal to or more than the threshold value, as a region indicating the bone. Additionally, the mask image generation unit 26 can detect, for example, blood vessels, bones, nerves, tendons, and the like, and then detect the remaining region as a region indicating muscle fibers.

Generally, since the cross section of the blood vessel and the cross section of a nerve bundle are observed as approximately circular regions, the mask image generation unit 26 can detect the blood vessel and the nerve bundle, for example, using Hessian-matrix H of the following Expression (1).

$$H = \begin{bmatrix} L_{xx} & L_{xy} \\ L_{xy} & L_{yy} \end{bmatrix} \quad (1)$$

Here, with $G(\sigma)$ being Gaussian filter with a standard deviation $\sigma$ and I being an input image, and $L_{xx}$, $L_{xy}$, and $L_{yy}$ are expressed by the following Expressions (2), (3), and (4), respectively.

$$L_{xx} = \frac{\partial^2}{\partial x^2} G(\sigma) * I \quad (2)$$

$$L_{xy} = \frac{\partial^2}{\partial x \partial y} G(\sigma) * I \quad (3)$$

$$L_{yy} = \frac{\partial^2}{\partial y^2} G(\sigma) * I \quad (4)$$

Generally, the more the regions having an isotropic shape, the more a determinant, that is, $L_{xx} \cdot L_{yy} - (L_{xy})^2$ of the Hessian-matrix H, which are expressed by Expression (1), has a positive large value. Therefore, the mask image generation unit 26 can detect, for example, a region where the determinant of the Hessian-matrix H is equal to or more than a predetermined positive threshold value as a region indicating the blood vessel or the nerve bundle.

Additionally, usually, a tendon is often observed as a structure having the high luminance in a shallow part of the ultrasound image. Therefore, the mask image generation unit 26 can detect, for example, a region that is shallower than the predetermined depth in the ultrasound image and has the luminance equal to or more than the threshold value, as a region indicating the tendon.

As illustrated in FIG. 11, the tomographic plane determination unit 13 of the processor 20A determines whether the tomographic plane of the subject depicted from the reference image and the tomographic plane of the subject depicted from the ultrasound image of the current frame are the same as each other by comparing the mask image C2 for reference image with the mask image D2 for the deformed image, which are generated by the mask image generation unit 26.

In this case, for example, the tomographic plane determination unit 13 can calculate the similarity between mask image C2 for the reference image and the mask image D2 for the deformed image, can determine that the tomographic plane of the subject depicted from the ultrasound image of the current frame and the tomographic plane of the subject depicted from the reference image are the same as each other in a case where the calculated similarity is equal to or more than a threshold value, and can determine that the tomographic plane of the subject depicted from the ultrasound image of the current frame and the tomographic plane of the subject depicted from the reference image are different from each other in a case where the similarity is smaller than the threshold value.

In this way, since the deformed image and the reference image can be compared with each other while paying attention to at least one of the muscle fibers or the bone by comparing the mask image C2 for the reference image with the mask image D2 for the deformed image, the determination of the tomographic plane is more easily and accurately performed.

Figure 12:
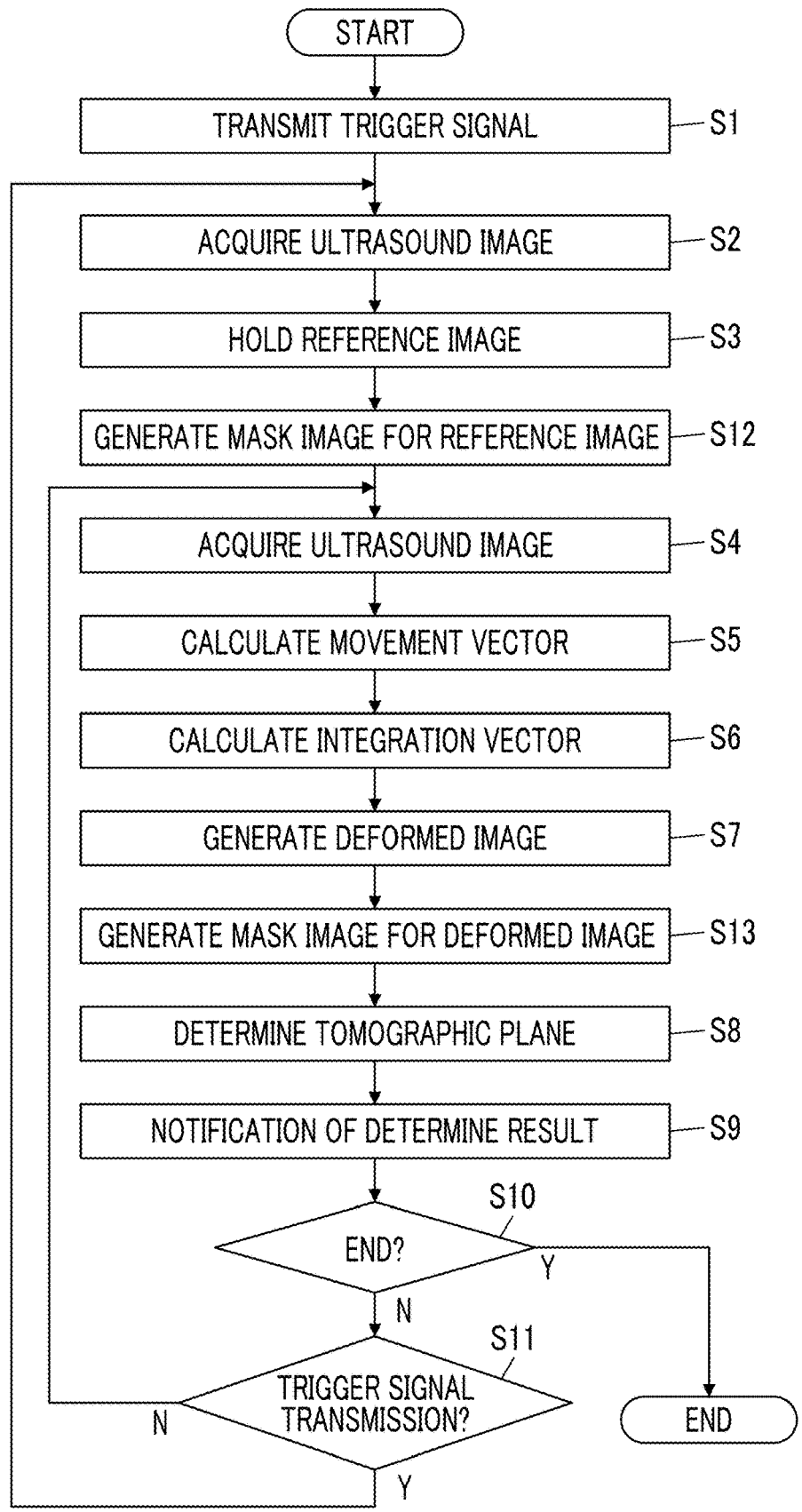
FIG. 12 is a flowchart illustrating an operation of the ultrasound diagnostic apparatus according to Embodiment 2 of the present invention.

Next, the operation of the ultrasound diagnostic apparatus 1A of Embodiment 2 will be described using the flowchart illustrated in FIG. 12. The flowchart of FIG. 12 is obtained by adding Step S12 between Step S3 and Step S4 and adding Step S13 between Step S7 and Step S8 in the flowchart of Embodiment 1 illustrated in FIG. 10.

First, in Step S1, in a case where the information indicating that the trigger signal is to be transmitted is input by the user via the input unit 17, the trigger signal transmitting unit 15 transmits the trigger signal to the reference image holding unit 9 and the movement vector integration unit 11.

In Step S2, the image acquisition unit 8 acquires the ultrasound image. In the following Step S3, the reference image holding unit 9 holds the ultrasound image acquired in Step S2 as the reference image.

In the following Step S12, the mask image generation unit 26 detects at least one of muscle fibers or the bone with respect to the ultrasound image held as the reference image in Step S3 and generates the mask image C2 in which regions other than the detected muscle fibers and the detected bone are masked.

In Step S4, the image acquisition unit 8 acquires the ultrasound image in the same manner as Step S2.

In Step S5, the movement vector calculation unit 10 calculates the movement vector indicating the image movement change between two ultrasound images by performing the image analysis with respect to two ultrasound images of the ultrasound image acquired in Step S2 and the ultrasound image acquired in Step S4.

In Step S6, the movement vector integration unit 11 integrates the movement vector calculated in Step S5. At the current time, since the movement vector is calculated once in Step S5, the integration vector obtained in Step S6 is equal to the movement vector calculated in Step S5.

In Step S7, the deformed image generation unit 12 generates the deformed image in which the ultrasound image acquired in Step S4 is moved and changed tracing back to the time when the reference image is acquired in Step S3, based on the image movement change integrated in Step S6.

In Step S13, the mask image generation unit 26 detects at least one of muscle fibers or the bone with respect to the deformed image generated in Step S7 in the same manner as Step S12, and generates the mask image D2 in which regions other than the detected muscle fibers and the detected bone are masked.

In Step S8, the tomographic plane determination unit 13 determines whether the tomographic plane of the subject depicted from the reference image and the tomographic plane of the subject depicted from the ultrasound image of the current frame are the same as each other by comparing the mask image C2, for the reference image, generated in Step S12 with the mask image D2, for the deformed image, generated in Step S13.

In Step S9, the determination result notification unit 14 notifies the user of the determination result obtained in Step S8.

In Step S10, it is determined whether the operation of the ultrasound diagnostic apparatus 1A is to be ended. Here, in a case where it is determined that the operation of the ultrasound diagnostic apparatus 1A is not ended, the process proceeds to Step S11.

In Step S11, it is determined whether the trigger signal is newly transmitted by the trigger signal transmitting unit 15. In a case where the trigger signal is not transmitted from the trigger signal transmitting unit 15 by the operation of the user via the input unit 17, it is determined that the trigger signal is not newly transmitted in Step S11, and the processing in Step S4 to Step S7, Step S13, and Step S8 to Step S11 is performed. In a case where the trigger signal is transmitted from the trigger signal transmitting unit 15 to the reference image holding unit 9 and the movement vector integration unit 11 by the operation of the user via the input unit 17, it is determined that the trigger signal is newly transmitted in Step S11, and the process returns to Step S2.

In a case where the ultrasound image is newly acquired by the image acquisition unit 8 in Step S2, and the ultrasound image acquired in the Step S2 is newly held by the reference image holding unit 9 as the reference image in Step S3, the mask image C2 for the reference image newly held in Step S3 is generated in Step S12. In a case where the process in Step S12 is completed, the processes in Step S4 to Step S7, Step S13, and Step S8 to Step S11 are performed again.

Additionally, in Step S10, in a case where it is determined that the operation of the ultrasound diagnostic apparatus 1A is to be ended, the operation of the ultrasound diagnostic apparatus 1A is ended.

According to the ultrasound diagnostic apparatus 1A of Embodiment 2 as described above, the deformed image can be compared with the reference image while paying attention to at least one of the muscle fibers or the bone in which a change of a structure pattern in the ultrasound image is particularly remarkable with respect to a change of the tomographic plane depicted from the ultrasound image, by comparing the mask image C2 for the reference image and the mask image D2 for the deformed image. Therefore, determination of the tomographic planes can be more easily and accurately performed.

In addition, in Embodiment 2, the mask image generation unit 26 detects at least one of the muscle fibers or the bone with respect to each of the deformed image and the ultrasound image of the current frame, and generates the mask images C2 and D2 in which the regions other than the muscle fibers and the bone are masked. However, for example, the mask image generation unit 26 can generate the mask image C2 for the ultrasound image of the current frame by applying the same mask as the mask for the deformed image to the ultrasound image of the current frame instead of generating the mask for the ultrasound image of the current frame. Additionally, the mask image generation unit 26 can also generate, for example, the mask image D2 for the deformed image by applying the same mask as the mask for the ultrasound image of the current frame to the deformed image instead of generating the mask for the deformed image.

Additionally, in Embodiment 2, although the mask image generation unit 26 generates the mask images C2 and D2 in which the regions other than the detected muscle fibers and the detected bone are masked, the mask images C2 and D2 are not limited to this. For example, also regarding the nerve bundle, in a case where the tomographic plane of the subject depicted from the ultrasound image changes, the structure pattern of the nerve bundle expressed by pixels with high luminance changes markedly. Therefore, the mask image generation unit 26 can generate the mask images C2 and D2 in which the nerve bundle is not masked. Although the mask image generation unit 26 detects the blood vessel and the nerve bundle using the Hessian-matrix H in Embodiment 2, generally, the nerve bundle is depicted from pixels having a luminance higher than that of the blood vessel. Therefore, for example, the mask image generation unit 26 can detect a region of which the luminance is equal to or more than the threshold value among the regions detected using the Hessian-matrix H, as the nerve bundle. However, usually, there is a case where the region of the nerve bundle is smaller than the region of the muscle fibers and the bone, and is not clearly depicted depending on the tomographic plane. Therefore, as the mask images C2 and D2, the mask image in which the regions other than the muscle fibers and the bone are masked is preferable.

Additionally, in Embodiment 2, the mask image generation unit 26 detects the region indicating the bone by comparing the luminance in the ultrasound image with a threshold value, detects regions indicating the blood vessel, the nerve bundle, the tendon, and the like, and detects the remaining region as a region indicating the muscle fibers. However the method of detecting the bone and the muscle fibers is not particularly limited to this. For example, the mask image generation unit 26 can learn features of the bones and the muscle fibers using general image recognition techniques, such as a machine learning technique and deep learning, and can also detect regions indicating the bone and the muscle fibers.

Embodiment 3

In Embodiment 2, although the mask image is generated with respect to the deformed image generated by the deformed image generation unit 12, a mask image can also be generated with respect to all ultrasound images acquired by the image acquisition unit 8, and a movement vector can also be calculated with respect to the generated mask image.

Figure 13:
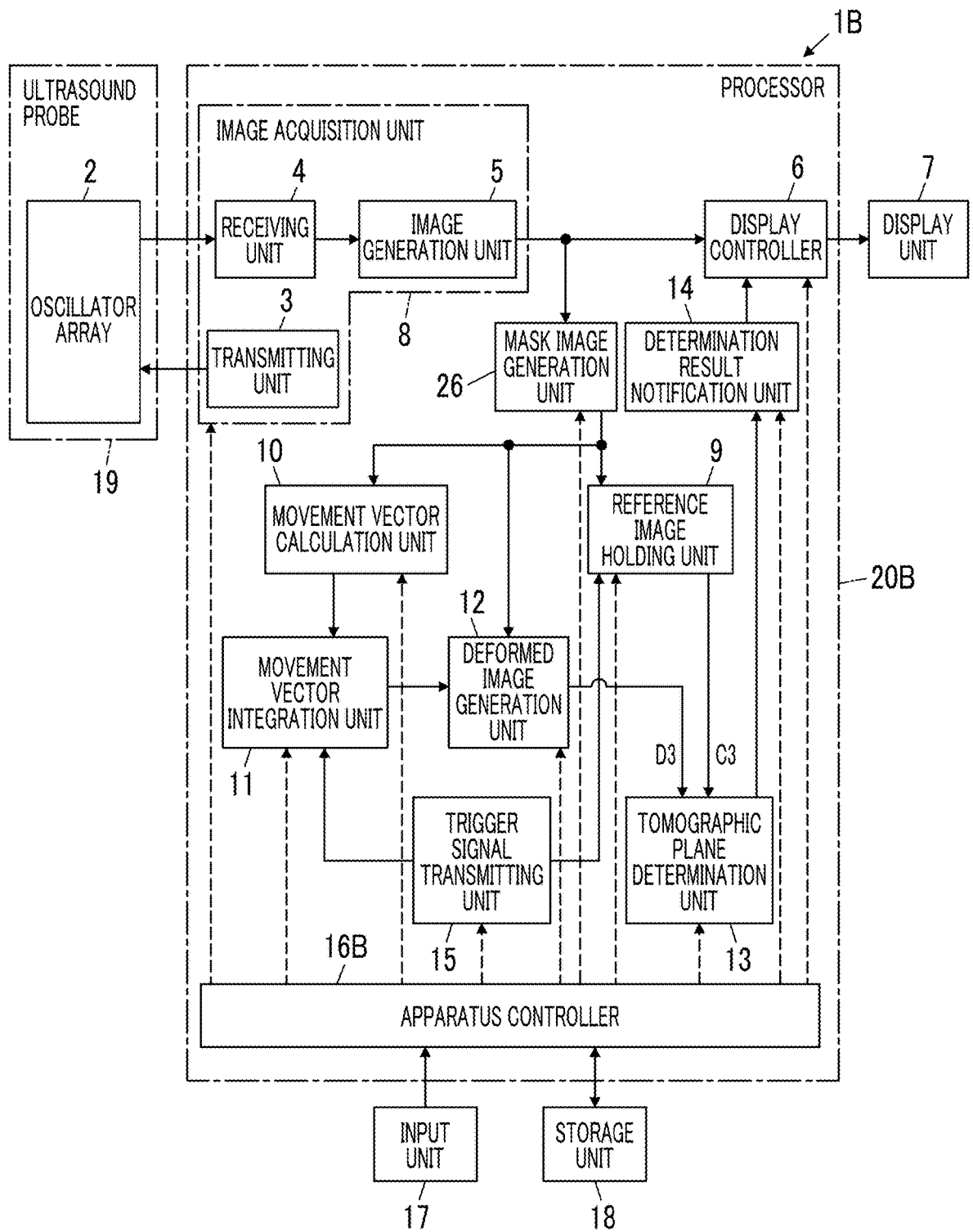
FIG. 13 is a block diagram illustrating a configuration of an ultrasound diagnostic apparatus according to Embodiment 3 of the present invention.

The configuration of an ultrasound diagnostic apparatus 1B according to Embodiment 3 is illustrated in FIG. 13. The ultrasound diagnostic apparatus 1B of Embodiment 3 comprises an apparatus controller 16B instead of the apparatus controller 16A in the ultrasound diagnostic apparatus 1A of Embodiment 2 illustrated in FIG. 11, and is an apparatus in which the connection relationship between the mask image generation unit 26, the reference image holding unit 9, and the deformed image generation unit 12 is changed.

In the ultrasound diagnostic apparatus 1B of Embodiment 3, the mask image generation unit 26 is connected to the image generation unit 5, and the reference image holding unit 9, the movement vector calculation unit 10, and the deformed image generation unit 12 are connected to the mask image generation unit 26. The tomographic plane determination unit 13 is connected to the reference image holding unit 9 and the deformed image generation unit 12. Additionally, the apparatus controller 16B is connected to the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the mask image generation unit 26.

Moreover, a processor 20B is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, the apparatus controller 16B, and the mask image generation unit 26.

Similarly to the mask image generation unit in Embodiment 2, the mask image generation unit 26 of the processor 20B detects at least one of the muscle fibers or the bone with respect to the ultrasound image acquired by the image acquisition unit 8, and generates the mask image in which regions other than the muscle fibers and the bone are masked.

The reference image holding unit 9 of the processor 20B holds the mask image generated by the mask image generation unit 26 as the reference image C3.

The movement vector calculation unit 10 of the processor 20B calculates the movement vector indicating an image movement change with respect to two consecutive mask images generated by the mask image generation unit 26.

The movement vector integration unit 11 of the processor 20B integrates the movement vector calculated by the movement vector calculation unit 10.

The deformed image generation unit 12 of the processor 20B generates the deformed image D3 in which the mask image generated for the ultrasound image of the current frame by the mask image generation unit 26 is moved and changed tracing back to a time when the reference image is held by the reference image holding unit 9, based on the movement change integrated by the movement vector integration unit 11.

As illustrated in FIG. 13, the tomographic plane determination unit 13 of the processor 20B determines whether the tomographic plane of the subject depicted from the reference image C3 and the tomographic plane of the subject depicted from the ultrasound image of the current frame are the same as each other, by comparing the deformed image D3 generated by the deformed image generation unit 12 with the reference image C3 held by the reference image holding unit 9.

Figure 14:
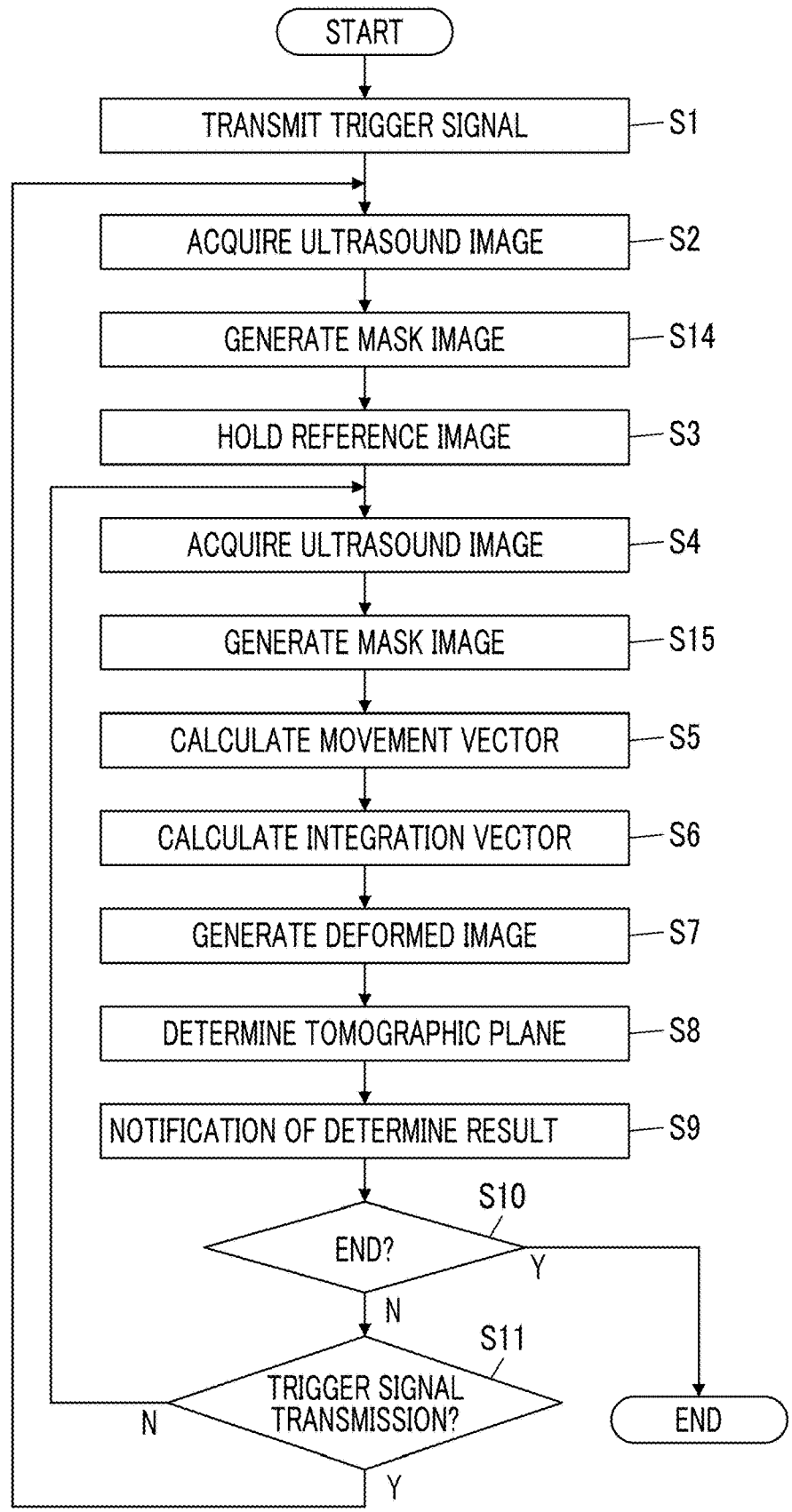
FIG. 14 is a flowchart illustrating the operation of the ultrasound diagnostic apparatus according to Embodiment 3 of the present invention.

Next, the operation of the ultrasound diagnostic apparatus 1B of Embodiment 3 will be described using the flowchart of FIG. 14. The flowchart of FIG. 14 is obtained by adding Step S14 between Step S2 and Step S3 and adding Step S15 between Step S4 and Step S5 in the flowchart of Embodiment 1 illustrated in FIG. 10.

First, in Step S1, in a case where the information indicating that the trigger signal is to be transmitted is input by the user via the input unit 17, the trigger signal transmitting unit 15 transmits the trigger signal to the reference image holding unit 9 and the movement vector integration unit 11.

In Step S2, the image acquisition unit 8 acquires the ultrasound image.

In the following Step S14, the mask image generation unit 26 detects at least one of the muscle fibers or the bone with respect to the ultrasound image acquired in Step S2, and generates the mask image in which regions other than the muscle fibers and the bone are masked.

In Step S3, the reference image holding unit 9 holds the mask image generated in Step S14 as the reference image C3.

In Step S4, the image acquisition unit 8 acquires the ultrasound image in the same manner as Step S2.

In Step S15, the mask image generation unit 26 generates the mask image with respect to the ultrasound image acquired in Step S4 in the same manner as Step S14.

In Step S5, the movement vector calculation unit 10 calculates the movement vector indicating the image movement change between two mask images by performing the image analysis with respect to two mask images of the mask image generated in Step S14 and the mask image generated in Step S15.

In Step S6, the movement vector integration unit 11 integrates the movement vector calculated in Step S5. At the current time, since the movement vector is calculated once in Step S5, the integration vector obtained in Step S6 is equal to the movement vector calculated in Step S5.

In Step S7, the deformed image generation unit 12 generates the deformed image D3 in which the mask image, for the ultrasound image of the current frame, generated in Step S15 is moved and changed tracing back to the time when the reference image C3 is held in Step S3, based on the movement change integrated in Step S6.

In Step S8, the tomographic plane determination unit 13 determines whether the tomographic plane of the subject depicted from the reference image C3 and the tomographic plane of the subject depicted from the ultrasound image of the current frame are the same as each other, by comparing the mask image, for the reference image C3, generated in Step S14 with the deformed image D3 generated in Step S7.

In Step S9, the determination result notification unit 14 notifies the user of the determination result obtained in Step S8.

In Step S10, it is determined whether the operation of the ultrasound diagnostic apparatus 1B is to be ended. Here, in a case where it is determined that the operation of the ultrasound diagnostic apparatus 1B is not ended, the process proceeds to Step S11.

In Step S11, it is determined whether the trigger signal is newly transmitted by the trigger signal transmitting unit 15. In a case where the trigger signal is not transmitted from the trigger signal transmitting unit 15 by the operation of the user via the input unit 17, it is determined that the trigger signal is not newly transmitted in Step S11, and the processing in Step S4, Step S15, and Step S5 to Step S11 is performed. In a case where the trigger signal is transmitted from the trigger signal transmitting unit 15 to the reference image holding unit 9 and the movement vector integration unit 11 by the operation of the user via the input unit 17, it is determined that the trigger signal is newly transmitted in Step S11, and the process returns to Step S2.

In a case where the ultrasound image is newly acquired by the image acquisition unit 8 in Step S2, the mask image for the ultrasound image acquired in Step S2 is generated by the mask image generation unit 26 in Step S14.

In the following Step S3, in a case where the mask image generated by the reference image holding unit 9 in Step S14 is newly held as the reference image C3, the processing in Step S4, Step S15, and Step S5 to Step S11 is performed again.

Additionally, in Step S10, in a case where it is determined that the operation of the ultrasound diagnostic apparatus 1B is to be ended, the operation of the ultrasound diagnostic apparatus 1B is ended.

As described above, according to the ultrasound diagnostic apparatus 1B of Embodiment 3, similarly to the ultrasound diagnostic apparatus 1A of Embodiment 2, the deformed image D3 can be compared with the reference image C3 while paying attention to at least one of the muscle fibers or the bone in which a change of structure patterns in the ultrasound image is particularly remarkable with respect to a change of the tomographic plane depicted from the ultrasound image. Therefore, determination of the tomographic plane can be more easily and accurately performed.

Embodiment 4

In Embodiment 1 to Embodiment 3, the trigger signal transmitting unit 15 transmits the trigger signal to the reference image holding unit 9 and the movement vector integration unit 11 by inputting the information indicating that the trigger signal is to be transmitted by the user via the input unit 17. However, the trigger signal can also automatically be transmitted.

Figure 15:
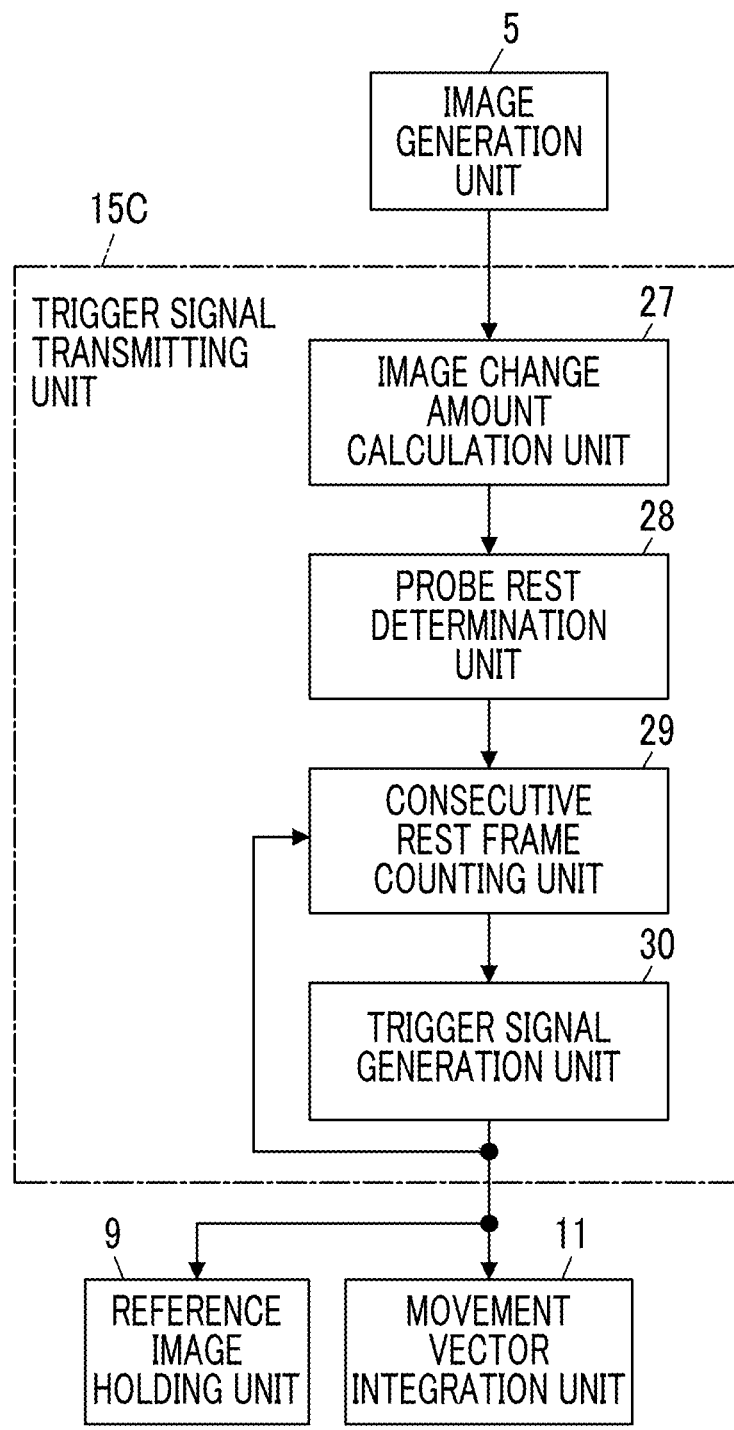
FIG. 15 is a block diagram illustrating an internal configuration of a trigger signal transmitting unit according to Embodiment 4 of the present invention.

An internal configuration of the trigger signal transmitting unit 15C in Embodiment 4 is illustrated in FIG. 15. As illustrated in FIG. 15, the trigger signal transmitting unit 15C has a configuration in which an image change amount calculation unit 27, a probe rest determination unit 28, a consecutive rest frame counting unit 29, and a trigger signal generation unit 30 are connected in series. Additionally, the image change amount calculation unit 27 is connected to the image generation unit 5. Additionally, the trigger signal generation unit 30 is connected to the consecutive rest frame counting unit 29 bi-directionally. Moreover, the trigger signal generation unit 30 is connected to the reference image holding unit 9 and the movement vector integration unit 11.

The trigger signal transmitting unit 15C performs the image analysis with respect to ultrasound images sequentially acquired by the image acquisition unit 8 to determine whether the ultrasound probe 19 is at rest, and automatically transmits the trigger signal to the reference image holding unit 9 and the movement vector integration unit 11 in a case where the ultrasound probe 19 is consecutive at rest, for example, only by the time corresponding to a predetermined number of frames of 15 to 30 frames.

Here, in a case where the compression test of the subject is performed, the user usually positions the ultrasound probe 19, and then presses the ultrasound probe 19 against the body surface of the subject to start the compression test. Moreover, in a case where the ultrasound probe 19 is positioned, there are many cases where the user makes the ultrasound probe 19 at rest. Therefore, the trigger signal is automatically transmitted to the reference image holding unit 9 and the movement vector integration unit 11 by the trigger signal transmitting unit 15C at a timing when the compression test is started.

The image change amount calculation unit 27 of the trigger signal transmitting unit 15C calculates the image change amount between two ultrasound images by performing the image analysis with respect to two consecutive ultrasound images generated by the image generation unit 5. Here, the image change amount is an index indicating how much images have changed, and can be calculated using a distance at which the images have moved between the two ultrasound images, an angle at which the images have rotated, or the like.

The probe rest determination unit 28 of the trigger signal transmitting unit 15C determines whether the ultrasound probe 19 is at rest based on the image change amount calculated by the image change amount calculation unit 27. For example, the probe rest determination unit 28 determines that the ultrasound probe 19 is at rest in a case where the image change amount calculated by the image change amount calculation unit 27 is equal to or less than a threshold value, and determines that the ultrasound probe 19 is moving in a case where the image change amount is larger than the threshold value.

In a case where the probe rest determination unit 28 determines that the ultrasound probe is moving, the image change amount is newly calculated by the image change amount calculation unit 27 with respect to the ultrasound image newly generated by the image generation unit 5, and the determination by the probe rest determination unit 28 is performed based on the calculated image change amount.

The consecutive rest frame counting unit 29 of the trigger signal transmitting unit 15C counts the number of consecutive ultrasound image frames that the probe rest determination unit 28 has determined that the ultrasound probe 19 is at rest.

In a case where the number of frames counted by the consecutive rest frame counting unit 29 reaches a predetermined number of frames, the trigger signal generation unit 30 of the trigger signal transmitting unit 15C generates the trigger signal, and transmits the generated trigger signal to the reference image holding unit 9, the movement vector integration unit 11, and the consecutive rest frame counting unit 29. In this way, in a case where the trigger signal is transmitted by the trigger signal generation unit 30, the reference image holding unit 9 eliminates the reference image held until now, the movement vector integration unit 11 eliminates the held integration vector, and the consecutive rest frame counting unit 29 eliminates the counted number of frames.

As described above, according to the ultrasound diagnostic apparatus according to Embodiment 4, the trigger signal transmitting unit 15C automatically transmits the trigger signal in a case where the ultrasound probe 19 is consecutively at rest by a predetermined number of frames. Therefore, the trigger signal is transmitted at a timing when the compression test is started, and the user's labor in the compression test can be mitigated.

In addition, the trigger signal transmitting unit 15C in Embodiment 4 is applicable to the ultrasound diagnostic apparatuses 1, 1A, and 1B of Embodiments 1 to 3.

EXPLANATION OF REFERENCES 1, 1A, 1B: ultrasound diagnostic apparatus
2: oscillator array
3: transmitting unit
4: receiving unit
5: image generation unit
6: display controller
7: display unit
8: image acquisition unit
9: reference image holding unit
10: movement vector calculation unit
11: movement vector integration unit
12: deformed image generation unit
13: tomographic plane determination unit
14: determination result notification unit
15, 15C: trigger signal transmitting unit
16, 16A, 16B: apparatus controller
17: input unit
18: storage unit
19: ultrasound probe
20, 20A, 20B: processor
21: amplification unit
22: AD conversion unit
23: signal processing unit
24: DSC
25: image processing unit
26: mask image generation unit
27: image change amount calculation unit
28: probe rest determination unit
29: consecutive rest frame counting unit
30: trigger signal generation unit
B: bone
BS: body surface
BV: blood vessel
C1, C3: reference image
D1, D3: deformed image
FP1, FP2: tomographic plane
C2, D2: mask image
MF: muscle fiber
R1, R2, R3: region
U1, U2, U3, U4: ultrasound image

What is claimed is:

1. An ultrasound diagnostic apparatus that has an ultrasound probe and is used to compression-test an observation target in a subject by pressing the ultrasound probe against a body surface of the subject, the ultrasound diagnostic apparatus comprising:
a processor configured to:
perform transmission of an ultrasound beam from the ultrasound probe toward the subject to acquire ultrasound images sequentially and consecutively;
display the ultrasound image that is acquired on a display;
hold the ultrasound image that is acquired in a state where a position of the ultrasound probe is fixed in order to depict a tomographic plane of the observation target on the display as a reference image;
calculate a movement vector indicating an image movement change between two ultrasound images that are consecutive for each predetermined number of frames among the ultrasound images that are sequentially acquired;
integrate the movement vectors that are respectively calculated in the ultrasound images from a time when the reference image is held to a current time;
generate a deformed image in which the ultrasound image of a current frame is moved and changed tracing back to a time when the reference image is held based on a movement change that is integrated by the movement vector integration unit;
determine whether a tomographic plane of the subject depicted from the ultrasound image of the current frame and a tomographic plane of the subject depicted from the reference image are the same as each other by comparing the deformed image that is generated with the reference image that is held; and
notify a user of a determination result that is obtained.

2. The ultrasound diagnostic apparatus according to claim 1,
wherein the processor is further configured to calculate a movement change of each pixel in the ultrasound image as the movement vector.

3. The ultrasound diagnostic apparatus according to claim 2,
wherein the processor is further configured to:
integrate the movement vector for each pixel with respect to the ultrasound images of a plurality of frames that is acquired; and
generate the deformed image by moving and changing each pixel in the ultrasound image of the current frame tracing back to a time when the reference image is held based on a movement change that is integrated.

4. The ultrasound diagnostic apparatus according to claim 1,
wherein the processor is further configured to calculate a movement change of a high-luminance pixel of which a luminance is equal to or more than a predetermined threshold value among all the pixels in the ultrasound image as the movement vector.

5. The ultrasound diagnostic apparatus according to claim 4,
wherein the processor is further configured to:

integrate the movement vector for each high-luminance pixel with respect to the ultrasound images of a plurality of frames that is acquired; and generate the deformed image based on a movement change of each high-luminance pixel in the ultrasound image of the current frame.

6. The ultrasound diagnostic apparatus according to claim 1, wherein the processor is further configured to partition the ultrasound images adjacent to each other in time series into a predetermined number of regions, respectively, and calculate a movement change of one pixel in each of the regions as the movement vector of the region.

7. The ultrasound diagnostic apparatus according to claim 6, wherein the processor is further configured to:

integrate the movement vector for each of the regions that are partitioned in the ultrasound images of the plurality of frames that are acquired; and generate the deformed image based on a movement change of each of the regions in the ultrasound image of the current frame.

8. The ultrasound diagnostic apparatus according to claim 7, wherein the processor is further configured to:

compare the deformed image with the reference image for each region that is partitioned to determine the tomographic plane of the subject; and notify the user of the determination result for each region that is obtained.

9. The ultrasound diagnostic apparatus according to claim 1, wherein the processor is further configured to perform image analysis with respect to the deformed image and the reference image to calculate a similarity between the deformed image and the reference image, and determine the tomographic plane of the subject based on the calculated similarity.

10. The ultrasound diagnostic apparatus according to claim 2, wherein the processor is further configured to image analysis with respect to the deformed image and the reference image to calculate a similarity between the deformed image and the reference image, and determine the tomographic plane of the subject based on the calculated similarity.

11. The ultrasound diagnostic apparatus according to claim 3, wherein the processor is further configured to perform image analysis with respect to the deformed image and the reference image to calculate a similarity between the deformed image and the reference image, and determine the tomographic plane of the subject based on the calculated similarity.

12. The ultrasound diagnostic apparatus according to claim 4, wherein the processor is further configured to perform image analysis with respect to the deformed image and the reference image to calculate a similarity between the deformed image and the reference image, and determine the tomographic plane of the subject based on the calculated similarity.

13. The ultrasound diagnostic apparatus according to claim 1, wherein the processor is further configured to superimpose the determination result that is obtained on the ultrasound image of the current frame to display the superimposed image on the display.

14. The ultrasound diagnostic apparatus according to claim 1, the processor is further configured to perform image analysis with respect to the deformed image that is generated and the reference image that is held to detect at least one of muscle fibers or a bone, and generate a mask image in which regions other than the muscle fibers and the bone respectively detected with respect to the deformed image and the reference image are masked.

15. The ultrasound diagnostic apparatus according to claim 14, wherein the processor is further configured to determine the tomographic plane of the subject by comparing the mask image for the deformed image with the mask image for the reference image.

16. The ultrasound diagnostic apparatus according to claim 1, wherein the processor is further configured to:

perform image analysis with respect to the ultrasound images, which are sequentially and consecutively acquired to detect at least one of muscle fibers or a bone, and generate a mask image in which regions other than the muscle fibers and the bone detected with respect to the ultrasound image are masked;

hold the mask image that is generated at a time when the position of the ultrasound probe is fixed in order to depict the tomographic plane of the observation target on the display , as the reference image;

calculate an image movement change in the mask image as the movement vector; and generate the deformed image in which the ultrasound image of the current frame is moved and changed tracing back to the time when the reference image is held based on a movement change of at least one of the muscle fibers or the bone that is integrated.

17. The ultrasound diagnostic apparatus according to claim 16, wherein the processor is further configured to determine the tomographic plane of the subject by comparing the deformed image with a mask image held as the reference image.

18. The ultrasound diagnostic apparatus according to claim 1, further comprising an input unit that allows the user to perform an input operation, wherein the processor is further configured to transmit a trigger signal in a case where information indicating that the trigger signal instructing to start a new operation is to be transmitted is input by the user via the input unit.

19. The ultrasound diagnostic apparatus according to claim 1, wherein the processor is further configured to:

perform image analysis with respect to the ultrasound images that are acquired sequentially and consecutively to calculate an image change amount obtained from at least one of an image movement distance between two consecutive ultrasound images or an image rotational amount between two consecutive ultrasound images; and transmit a trigger signal instructing to start a new operation in a case where the ultrasound images of which the image change amount is equal to or less than a predetermined threshold value are consecutively acquired by a predetermined number of frames.

20. A method of controlling an ultrasound diagnostic apparatus that is used to compression-test an observation target in a subject by pressing an ultrasound probe against a body surface of the subject, the method comprising:

performing transmission of an ultrasound beam toward the subject to acquire ultrasound images sequentially and consecutively;

holding the ultrasound image acquired in a state where a position of the ultrasound probe is fixed in order to depict a tomographic plane of the observation target as a reference image;

calculating a movement vector indicating an image movement change between two ultrasound images that are consecutive for each predetermined number of frames among the sequentially acquired ultrasound images;

integrating the movement vectors that are respectively calculated in the ultrasound images from a time when the reference image is held to a current time;

generating a deformed image in which the ultrasound image of a current frame is moved and changed tracing back to a time when the reference image is held based on the integrated movement change;

determining whether a tomographic plane of the subject depicted from the ultrasound image of the current frame and a tomographic plane of the subject depicted from the reference image are the same as each other by comparing the generated deformed image with the held reference image; and notifying a user of a determination result.

* * * * *